(12) United States Patent
Huber

(10) Patent No.: US 8,182,530 B2
(45) Date of Patent: May 22, 2012

(54) METHODS AND DEVICES FOR REPAIR OR REPLACEMENT OF HEART VALVES OR ADJACENT TISSUE WITHOUT THE NEED FOR FULL CARDIOPULMONARY SUPPORT

(76) Inventor: Christoph Hans Huber, Lausanne (CH)

( * ) Notice: Subject to any disclaimer, the term of this patent is extended or adjusted under 35 U.S.C. 154(b) by 1552 days.

(21) Appl. No.: 11/023,783

(22) Filed: Dec. 28, 2004

(65) Prior Publication Data

US 2006/0074484 A1    Apr. 6, 2006

Related U.S. Application Data

(60) Provisional application No. 60/615,009, filed on Oct. 2, 2004.

(51) Int. Cl.
*A61F 2/24*     (2006.01)
*A61B 17/3205*  (2006.01)

(52) U.S. Cl. ...................................... 623/2.11; 128/898

(58) Field of Classification Search ................. 623/2.11, 623/2.1, 1.11; 606/139, 144–148, 166, 184–185, 606/191–192, 194; 128/898
See application file for complete search history.

(56) References Cited

U.S. PATENT DOCUMENTS

| | | | |
|---|---|---|---|
| 832,201 A | 10/1906 | Kistler | |
| 1,331,737 A | 2/1920 | Ylisto | |
| 3,671,979 A | 6/1972 | Moulopoulos | |
| 4,056,854 A | 11/1977 | Boretos et al. | |
| 4,327,736 A | 5/1982 | Inoue | |
| 4,343,048 A | 8/1982 | Ross et al. | |
| 4,585,000 A | 4/1986 | Hershenson | |
| 4,777,951 A | 10/1988 | Cribier et al. | |
| 5,332,402 A | 7/1994 | Teitelbaum | |
| 5,397,351 A | 3/1995 | Pavcnik et al. | |
| 5,792,094 A | 8/1998 | Stevens et al. | |
| 5,840,081 A | 11/1998 | Andersen et al. | |
| 5,855,597 A | 1/1999 | Jayaraman | |
| 5,873,366 A * | 2/1999 | Chim et al. .................... | 128/898 |
| 5,895,399 A | 4/1999 | Barbut et al. | |
| 5,957,949 A | 9/1999 | Leonhardt et al. | |

(Continued)

FOREIGN PATENT DOCUMENTS

WO    WO 00/47139    8/2000

(Continued)

OTHER PUBLICATIONS

Gibson, Mark A. and Carell, Edgar S., "Direct Right Ventricular Puncture for Hemodynamic Evaluation of a Mechanical Tricuspid Valve Prosthesis: A New Indication for an Old Procedure," Catheterization and Cardiovascular Diagnosis 42:278-282 (1997).

(Continued)

*Primary Examiner* — Corrine M McDermott
*Assistant Examiner* — Mark Mashack
(74) *Attorney, Agent, or Firm* — Weiss & Arons LLP

(57) ABSTRACT

Methods and systems for endovascular, endocardiac, or endoluminal approaches to a patient's heart to perform surgical procedures that may be performed or used without requiring extracorporeal cardiopulmonary bypass. Furthermore, these procedures can be performed through a relatively small number of small incisions. These procedures may illustratively include heart valve implantation, heart valve repair, resection of a diseased heart valve, replacement of a heart valve, repair of a ventricular aneurysm, repair of an arrhythmia, repair of an aortic dissection, etc. Such minimally invasive procedures are preferably performed transapically (i.e., through the heart muscle at its left or right ventricular apex).

16 Claims, 25 Drawing Sheets

U.S. PATENT DOCUMENTS

| | | | |
|---|---|---|---|
| 5,980,532 | A | 11/1999 | Wang |
| 6,168,614 | B1 | 1/2001 | Andersen et al. |
| 6,203,561 | B1 | 3/2001 | Ramee et al. |
| 6,338,740 | B1 | 1/2002 | Carpentier |
| 6,419,696 | B1 * | 7/2002 | Ortiz et al. ............... 623/2.37 |
| 6,425,916 | B1 * | 7/2002 | Garrison et al. ............ 623/2.11 |
| 6,458,153 | B1 | 10/2002 | Bailey et al. |
| 6,458,156 | B1 | 10/2002 | Wan et al. |
| 6,482,228 | B1 | 11/2002 | Norred |
| 6,503,272 | B2 | 1/2003 | Duerig et al. |
| 6,562,058 | B2 | 5/2003 | Seguin et al. |
| 6,569,196 | B1 | 5/2003 | Vesely |
| 6,620,182 | B1 | 9/2003 | Khosravi et al. |
| 6,663,651 | B2 | 12/2003 | Krolik et al. |
| 6,679,268 | B2 * | 1/2004 | Stevens et al. ............. 128/898 |
| 6,682,558 | B2 | 1/2004 | Tu et al. |
| 6,692,513 | B2 | 2/2004 | Streeter et al. |
| 6,726,702 | B2 | 4/2004 | Khosravi |
| 6,730,118 | B2 | 5/2004 | Spenser et al. |
| 6,733,525 | B2 | 5/2004 | Yang et al. |
| 6,764,494 | B2 | 7/2004 | Menz et al. |
| 6,767,362 | B2 | 7/2004 | Schreck |
| 6,840,246 | B2 | 1/2005 | Downing |
| 2003/0130571 | A1 * | 7/2003 | Lattouf ...................... 600/374 |
| 2004/0093060 | A1 * | 5/2004 | Seguin et al. ............... 623/1.11 |
| 2004/0118415 | A1 * | 6/2004 | Hall et al. .................... 128/898 |
| 2004/0210304 | A1 * | 10/2004 | Seguin et al. ............... 623/2.11 |
| 2005/0240200 | A1 * | 10/2005 | Bergheim .................... 606/108 |
| 2005/0251251 | A1 * | 11/2005 | Cribier ........................ 623/2.11 |
| 2006/0142848 | A1 * | 6/2006 | Gabbay ........................ 623/1.26 |
| 2007/0112422 | A1 * | 5/2007 | Dehdashtian ................ 623/2.11 |

FOREIGN PATENT DOCUMENTS

| | | |
|---|---|---|
| WO | WO 03/028592 | 4/2003 |
| WO | WO 2004/019811 | 3/2004 |

OTHER PUBLICATIONS

Huber, Christoph, et al., "Do valved stents compromise coronary flow?" European Journal of Cardio-thoracic Surgery, 25 (2004) 754-59.

Huber, Christoph, et al., "No drive line," Interactive Cardiovascular and Thoracic Surgery, 3 (2004) 336-40.

Huber, Christoph, et al., "Rupture of a Polypropylene Suture After Aortic Operation," Ann Thorac Surg, 2003, 75:1318-21.

Huber, Christoph, et al., "Ultrasound Navigation Through the Heart for Off-Pump Aortic Valved Stent Implantation," J Endovasc Ther, 2004, 11:503-10.

Khalaf, Salah A. and Mageed, Nabil A., "Intraoperative Hemodynamic Improvement After Closed Mitral Valvotomy," J. of Egypt. Society of Cardiothorac. Surg. 2002, vol. X April No. 2.

Morgan, J.M., et al., "Left Heart Catheterization by Direct Ventricular Puncture: Withstanding the Test of Time," Catheterization and Cardiovascular Diagnosis 16:87-90 (1989).

Ommen, S.R., et al., "Summary of the Mayo Clinic Experience with Direct Left Ventricular Puncture," Catheterization and Cardiovascular Diagnosis 44:175-178 (1998).

Patel, Jai J., et al., "Balloon Valvuloplasty Versus Closed Commissurotomy for Pliable Mitral Stenosis: A Prospective Hemodynamic Study," JACC, vol. 18, No. 5, Nov. 1, 1991:1318-22.

Sivasubramanian, Mani, "Mitral Stenosis," May 4, 1997. <http://www.heartdiseaseonline.com/aa/aa050497.htm>.

Von Segesser, L.K., et al., "Reparations endovasculaires des anevrismes aortiques," Med Hyg, 2003, 61:1134-38.

Wasir, H.S., et at, "Percutaneous Left Ventricular Puncture in Aortic Valve Disease," Indian Heart Journal, vol. 32, No. 2, 81-84, 1980.

Zhou, Jun Qing; Corno, Antonio; Huber, Christophe, et al., "Self-expandable valved stent of large size," European Journal of Cardio-thoracic Surgery, 24 (2003) 212-16.

* cited by examiner

METHODS AND DEVICES FOR REPAIR OR REPLACEMENT OF HEART VALVES OR ADJACENT TISSUE WITHOUT THE NEED FOR FULL CARDIOPULMONARY SUPPORT

This application claims the benefit of U.S. provisional patent application No. 60/615,009, filed Oct. 2, 2004, which is hereby incorporated by reference herein in its entirety.

FIELD OF THE INVENTION

This invention relates generally to devices and methods for performing cardiovascular procedures wherein a heart valve or segment of the aorta is being repaired or replaced without the use of extracorporeal cardiopulmonary support (commonly referred to as "off-pump" procedures). For example, the invention relates to devices and methods for accessing, resecting, repairing, and/or replacing one of the heart valves, in particular the aortic valve. This invention also relates to methods and systems for performing minimally-invasive cardiac procedures such as the endovascular, endocardiac or endoluminal placement, implantation or removal and consecutive replacement of heart valves. These techniques may be generally referred to as direct access percutaneous valve replacement ("DAPVR").

BACKGROUND OF THE INVENTION

Of particular interest to the present invention is the treatment of heart valve disease. There are two major categories of heart valve disease: (i) stenosis, which is an obstruction to forward blood flow caused by a heart valve, and (ii) regurgitation, which is the retrograde leakage of blood through a heart valve. Stenosis often results from calcification of a heart valve that makes the valve stiffer and less able to open fully. Therefore, blood must be pumped through a smaller opening. Regurgitation can be caused by the insufficiency of any of the valve leaflets such that the valve does not fully close.

In the past, repairing or replacing a malfunctioning heart valve within a patient has been achieved with a major open-heart surgical procedure, requiring general anesthesia and full cardiopulmonary by-pass. This requires complete cessation of cardiopulmonary activity. While the use of extracorporeal cardiopulmonary by-pass for cardiac support is a well accepted procedure, such use has often involved invasive surgical procedures (e.g., median sternotomies, or less commonly, thoracotomies). These operations usually require one to two weeks of hospitalization and several months of rehabilitation time for the patient. The average mortality rate with this type of procedure is about five to six percent, and the complication rate is substantially higher.

Endovascular surgical techniques for heart surgery have been under recent development. In contrast to open-heart surgical procedures, endovascular procedures may have a reduced mortality rate, may require only local anesthesia, and may necessitate only a few days of hospitalization. However, the range of procedures that has been developed for an endovascular approach to date has been limited to repair of the coronary arteries, such as angioplasty and atherectomy.

Some progress has been made in the development of endovascular heart valve procedures. For example, for patients with severe stenotic valve disease who are too compromised to tolerate open-heart surgery to replace the heart valve as described above, surgeons have attempted endovascular balloon aortic or mitral valvuloplasty. These procedures involve endovascularly advancing a balloon dilatation catheter into the patient's vasculature until the balloon of the catheter is positioned between the valve leaflets. Then the balloon is inflated to either: (i) split the commissures in a diseased valve with commissural fusion, or (ii) crack calcific plaques in a calcified stenotic valve. However, this method may only provide partial and temporary relief for a patient with a stenotic valve. Instances of restenosis and mortality following balloon aortic valvuloplasty have led to virtual abandonment of this procedure as a treatment for a diseased aortic valve.

Endovascular procedures for valve implantation inside a native and diseased valve have been explored. A catheter-mounted valve is incorporated into a collapsible cylindrical structure, such as a stent (commonly referred to as a "valved stent"). In these procedures, an elongated catheter is used to insert a mechanical valve into the lumen of the aorta via entry through a distal artery (e.g., the femoral or brachial artery). Such procedures have been attempted on selective, terminally ill patients as a means of temporarily relieving the symptoms of a diseased valve.

The percutaneous placement of an artificial valve may have certain limitations and ancillary effects. For example, at present, such procedures are only of benefit to a small number of patients and are not meant to become an alternative to surgical heart valve procedures requiring the use of extracorporeal bypass. Another issue is that performing the entire procedure via small diameter vessels (e.g., the femoral, iliac or brachial arteries) restricts the use of larger tools and devices for the resection or repair of the diseased heart valve. Furthermore, this endovascular procedure may increase the risk of various vascular complications such as bleeding, dissection, rupture of the blood vessel, and ischemia to the extremity supplied by the vessel used to perform the operation.

Moreover, in some cases, one or more of a patient's femoral arteries, femoral veins, or other vessels for arterial and venous access may not be available for introduction of delivery devices or valve removal tools due to inadequate vessel diameter, vessel stenosis, vascular injury, or other conditions. In such cases, there may not be sufficient arterial and venous access to permit the contemporaneous use of the necessary interventional devices (e.g., an angioplasty catheter, atherectomy catheter, or other device) for a single surgical procedure. Therefore, unless alternate arterial or venous access for one or more of these catheters can be found, the procedure cannot be performed using endovascular techniques.

Another possible disadvantage of the small vessel procedure is that the new valve must be collapsed to a very small diameter that could result in structural damage to the new valve. Additionally, such remote access sites like the femoral artery may make precise manipulation of the surgical tools more difficult (e.g., exchange of guide wires and catheters and deployment of the new valve). Furthermore, placing wires, catheters, procedural tools, or delivery devices through one or more heart structures (e.g., the mitral valve) to reach the target site can result in damage to those structures (e.g., acute malfunctioning or insufficiency of the valve being mechanically hindered by the surgical equipment or valve deterioration resulting from mechanical friction inflicting micro-lesions on the valve).

Also to be considered in connection with such procedures is the potential of obstructing the coronary ostia. The known percutaneous procedures for implanting heart valves do not have a safety mechanism to ensure proper orientation of the new valve. Therefore, there is a possibility that the deployed valve will obstruct the coronary ostia, which can result in myocardial ischemia, myocardial infarction, and eventually the patient's death.

These procedures leave the old valve in place, and the new valve is implanted within the diseased valve after the diseased valve has been compressed by a balloon or other mechanical device. Therefore, there may be a possibility of embolic stoke or embolic ischemia from valve or vascular wall debris that is liberated into the blood flow as the diseased valve is dilated and compressed. Furthermore, a rim of diseased tissue (e.g., the compressed native valve) decreases the diameter and cross-sectional surface of the implanted valve, potentially under-treating the patient and leading to only partial relief of his symptoms.

It would therefore be desirable to develop systems and methods for satisfactorily performing various cardiovascular procedures, particularly procedures for heart valve placement or removal and replacement, which do not require the use of an extracorporeal bypass or invasive surgical procedure, such as a sternotomy. It would be further desirable to perform such procedures through very small incisions in the patient (e.g., via several small thoracotomies). The devices and methods will preferably facilitate the access, resection, repair, implantation, and/or replacement of the diseased cardiac structure (e.g., one or more diseased heart valves). The devices and methods should preferably minimize the number of arterial and venous penetrations required during the closed-chest procedures, and desirably, should require no more than one cardiac and one femoral arterial penetration. The present invention satisfies these and other needs.

The descriptive terms antegrade and retrograde mean in the direction of blood flow and opposite the direction of blood flow, respectively, when used herein in relation to the patient's vasculature. In the arterial system, antegrade refers to the downstream direction (i.e., the same direction as the physiological blood flow), while retrograde refers to the upstream direction (i.e., opposite the direction of the physiological blood flow). The terms proximal and distal, when used herein in relation to instruments used in the procedure, refer to directions closer to and farther away from the heart, respectively. The term replacement normally signifies removal of the diseased valve and implantation of a new valve. However, a new valve may also be implanted directly over top of a diseased valve. An implantation procedure would be the same as a replacement procedure without the removal of the diseased valve.

SUMMARY OF THE INVENTION

The present invention is directed to a method and system for an endovascular, endocardiac, or endoluminal approach to a patient's heart to perform an operation that does not require an extracorporeal cardiopulmonary bypass circuit and that can be performed through a limited number of small incisions, thus eliminating the need for a sternotomy. The invention contemplates, at least in its preferred embodiments, the possibility of effective aortic valve implantation, aortic valve repair, resection of the aortic valve and replacement of the aortic valve, all without necessitating extracorporeal cardiopulmonary by-pass, a median sternotomy or other grossly thoracic incisions.

The present invention contemplates replacing any of the four valves of the heart via an antegrade approach through the wall of the appropriate chamber. Preferably, valves are implanted transapically (i.e., through the heart muscle at its left or right ventricular apex). However, in this case, replacement of the mitral and tricuspid valves may be performed via a retrograde approach, because accessing these valves via the left or right ventricles requires approaching these valves against the flow of blood through the valve.

In accordance with the present invention, a surgeon may perform a minimally invasive operation on a patient that includes accessing the patient's heart and installing an access device in a wall of the heart that has means for preventing bleeding through the access device. A new heart valve may be implanted via the access device. In addition to implanting a heart valve during such a procedure, the surgeon can also resect a diseased native heart valve. The surgeon may also repair an aortic dissection using such a procedure. The surgeon may also choose to repair a damaged heart valve using similar techniques. The access device described may be preferably installed in the ventricular apex of the heart.

Surgical methods in accordance with the present invention may also include resecting a diseased heart valve percutaneously, while installing the new heart valve transapically. Alternatively, a surgeon may resect a diseased valve transapically and implant a new valve percutaneously. Additionally, both removal and implantation could be performed transapically. The new heart valve is preferably implanted by radially expanding the heart valve. In some embodiments, the radial expansion occurs in multiple stages that may be effectuated by a multi-stage balloon. The implantation device may include a mechanism to pull the leaflets of a native valve downward while the new valve is installed within the native valve.

A device for resecting a diseased heart valve in accordance with the present invention may include a first set of annularly enlargeable componentry having a first longitudinal axis and a proximal cutting edge and a second set of annularly enlargeable componentry having a second longitudinal axis and a distal cutting edge. The device resects the diseased heart valve when the first set of componentry is enlarged on a distal side of the diseased heart valve and the second set of componentry is enlarged on a proximal side of the diseased heart valve and the sets of componentry are drawn axially together along the longitudinal axes. The first and second sets of annularly enlargeable componentry may be coaxial.

In accordance with the present invention, blood flow through the surgical devices placed in the patient (e.g., inside the patient's aorta) may be supplemented with artificial devices such as ventricular assist devices. The surgical site may be visualized with direct optical technology. For example, transparent oxygen-carrying fluid may be injected into a portion of the circulatory system of a patient, and an optical device may be inserted into the transparent fluid to transmit images of the surgical site. Using such techniques, all blood of a patient's circulatory system may be temporarily exchanged with the transparent oxygen-carrying fluid.

Instrumentation for accessing a chamber of a patient's heart may include a catheter having a proximal sealing device for sealing the catheter against a proximal surface of the myocardium. The instrumentation may also include means for preventing bleeding through the catheter. In some embodiments, the instrumentation includes a distal sealing device for sealing the catheter against the distal surface of the myocardium.

In accordance with the present invention, an implantable heart valve may include a tissue support structure and tissue valve leaflets that are grown inside the tissue support structure by genetic engineering. The genetically engineered leaflets may grow inside a stainless steel stent, a nitinol stent, or any other suitable tissue support structure. Low-profile heart valves may also be used that include at least three leaflets. One side of each leaflet overlaps a neighboring leaflet such that the leaflets open sequentially and close sequentially. Replacement heart valves may also be used that correct overly-dilated heart valve annuluses. Such a heart valve may include an inner circumference defined by the leaflets of the heart valve and an outer circumference defined by the outer limits of a fluid-tight diaphragm. The diaphragm fills the space between the inner circumference and the outer circumference.

Surgeons may be aided by a device for inserting more than one guidewire into a patient. Such a device includes an annular wire placement device and one or more guidewires removably attached to the annular wire placement device. The annular wire placement device is configured to track an already placed guidewire.

In accordance with the present invention, calcification of a heart valve may be broken down by inserting a catheter-based ultrasound device into a calcified heart valve and concentrating ultrasound radiation on the calcification of the calcified heart valve to break down the calcification. Such a procedure may be enhanced by inserting a reflector into the calcified heart valve to magnify the ultrasound radiation.

A mitral valve repair device in accordance with the present invention may include a first head defining an operating plane and a second head operably attached to the first head. The second head is configured to displace a leaflet with respect to the operating plane. The first head may be U-shaped and include an attachment mechanism for attaching at least two portions of a mitral valve leaflet. The repair device includes a handle for operating the second head with respect to the first head.

In accordance with the present invention, aortic dissections may be repaired by accessing a patient's heart and placing an access device in a wall of the heart that prevents bleeding through the access device. A dissection repair device is inserted through the access device to repair the aortic dissection. The device may include annularly enlargeable componentry configured to be inserted into the patient's aorta and means for closing a void created by the aortic dissection. The void can be closed by injecting a biologically compatible glue (e.g., fibrin, thrombin, or any other suitable chemical or biological substance) through needles into the void. It may also be closed using mechanical sutures or surgical staples, for example.

BRIEF DESCRIPTION OF THE DRAWINGS

Further features of the invention, its nature, and various advantages will be more apparent from the following detailed description and the accompanying drawings, wherein like reference characters represent like elements throughout, and in which.

DETAILED DESCRIPTION OF THE PREFERRED EMBODIMENTS

Because the present invention has a number of different applications, each of which may warrant some modifications of such parameters as instrument size and shape, it is believed best to describe certain aspects of the invention with reference to relatively generic schematic drawings. To keep the discussion from becoming too abstract, however, and as an aid to better comprehension and appreciation of the invention, references will frequently be made to specific uses of the invention. Most often these references will be to use of the invention to resect and replace or implant an aortic valve with an antegrade surgical approach. It is emphasized again, however, that this is only one of many possible applications of the invention.

Figure 1:
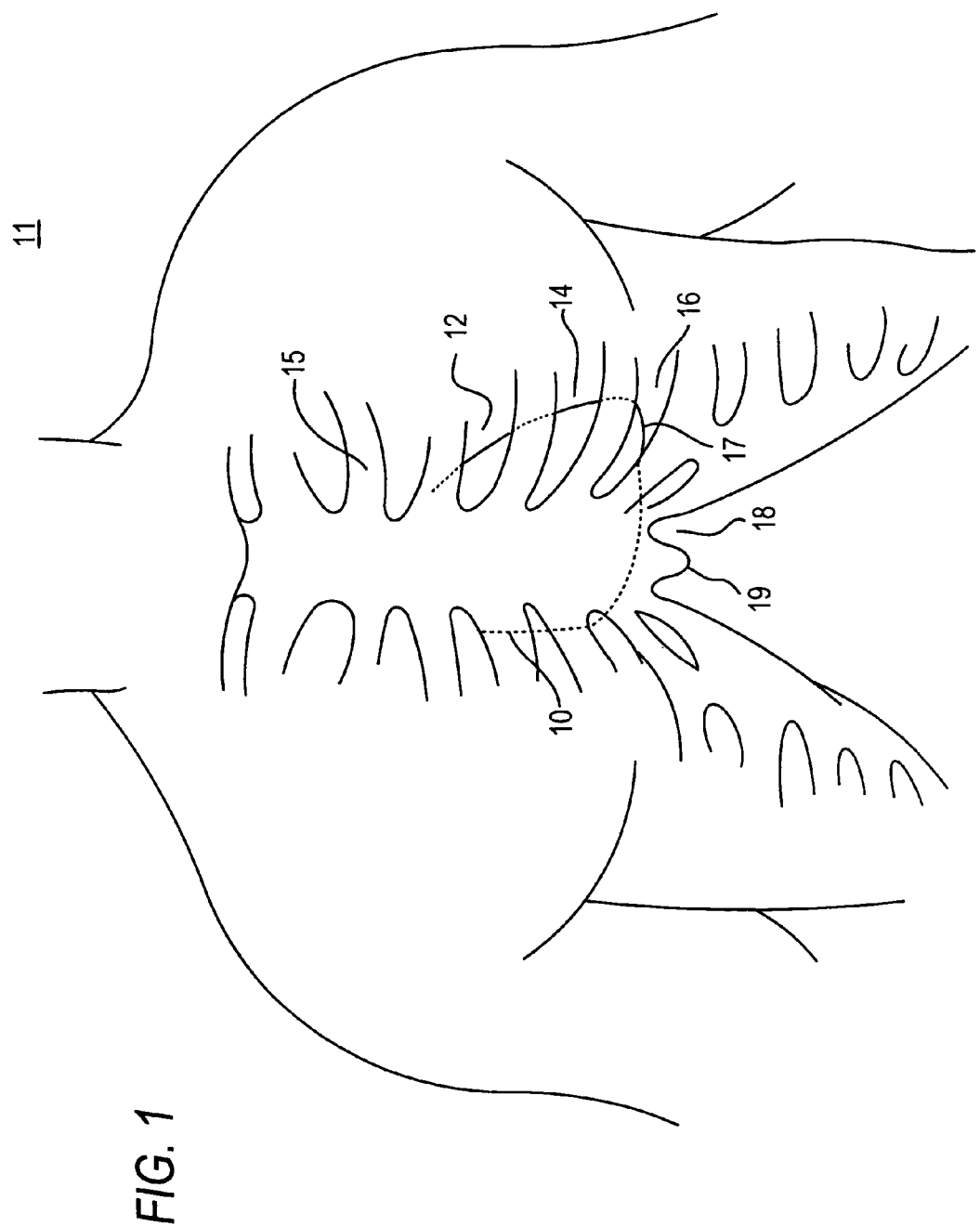
FIG. 1 is a view of a surgical site in accordance with the principles of the present invention.

Assuming that the invention is to be used to resect and replace or implant an aortic valve, the procedure may begin by setting up fluoroscopy equipment to enable the surgeon to set and use various reference points during the procedure. The surgeon may begin by performing a thoracotomy to create an access site for the surgical procedure. The endovascular, endocardiac or endoluminal surgical system of the present invention incorporates accessing the interior of the heart by directly penetrating the heart muscle, preferably through the heart muscle at its left or right ventricular apex (hereinafter referred to as "transapically"). Thoracotomy sites may be prepared at any of third intercostal space 12, fourth intercostal space 14, fifth intercostal space 16, or subxyphoidal site 18 (i.e., just below xyphoid process 19) of patient 11, as shown in FIG. 1. Any intercostal space may serve as a suitable surgical site, and in some embodiments of the present invention, the fourth, fifth, or sixth intercostal spaces are the preferred sites. All of these sites provide surgical access to apex 17 of heart 10. A 5-10 cm incision at any one of these sites may allow the surgeon to perform the entire procedure through one access site. However, alternatively, the surgeon may prefer to use an endoscopic technique wherein he or she may utilize 1-3 cm incisions at multiple sites to insert various instruments.

Once the heart is exposed, the surgeon may place one or multiple purse-string sutures around the ventricular apex surgical site. This will allow the surgeon to synch the heart muscle around any equipment that is passed through the heart wall during surgery to prevent bleeding. Other techniques for preventing bleeding from the heart chamber that is accessed for surgery will be described in more detail below.

Figure 2:
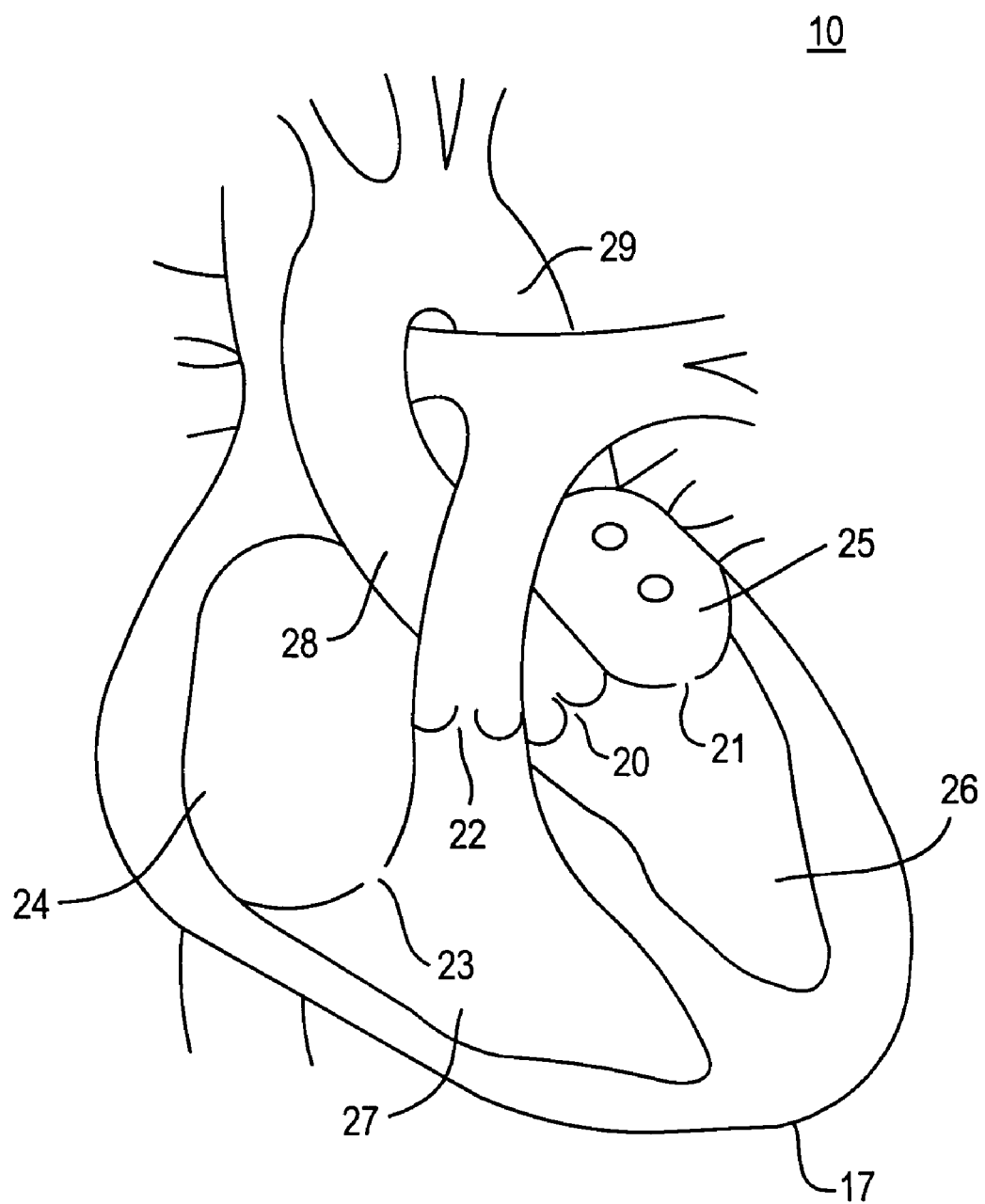
FIG. 2 is a detailed cut-away view of a portion of the surgical site illustrated in FIG. 1.

FIG. 2 illustrates the four chambers of heart 10: right atrium 24, left atrium 25, left ventricle 26, and right ventricle 27. FIG. 2 also shows the four valves of heart 10: aortic valve 20, mitral valve 21, pulmonary valve 22, and tricuspid valve 23. Ascending aorta 28 and descending aorta 29 are also illustrated. A procedure to replace aortic valve 20 may require a left thoracotomy and a left transapical incision to the heart muscle. Alternatively, a procedure to replace pulmonary valve 22 may require a right thoracotomy and a right transapical incision to the heart muscle. Direct access may be made via incisions to right and left atria 24 and 25 as well to enable antegrade approaches to tricuspid valve 23 and mitral valve 21. While the procedure may be used for antegrade and retrograde repair to any of a patient's heart valves, the following illustrative procedure relates to the resection and antegrade replacement of aortic valve 20. It should be understood that the resection steps may be skipped in the following procedure, and a replacement valve may alternatively be placed concentrically within the diseased valve.

Figure 3:
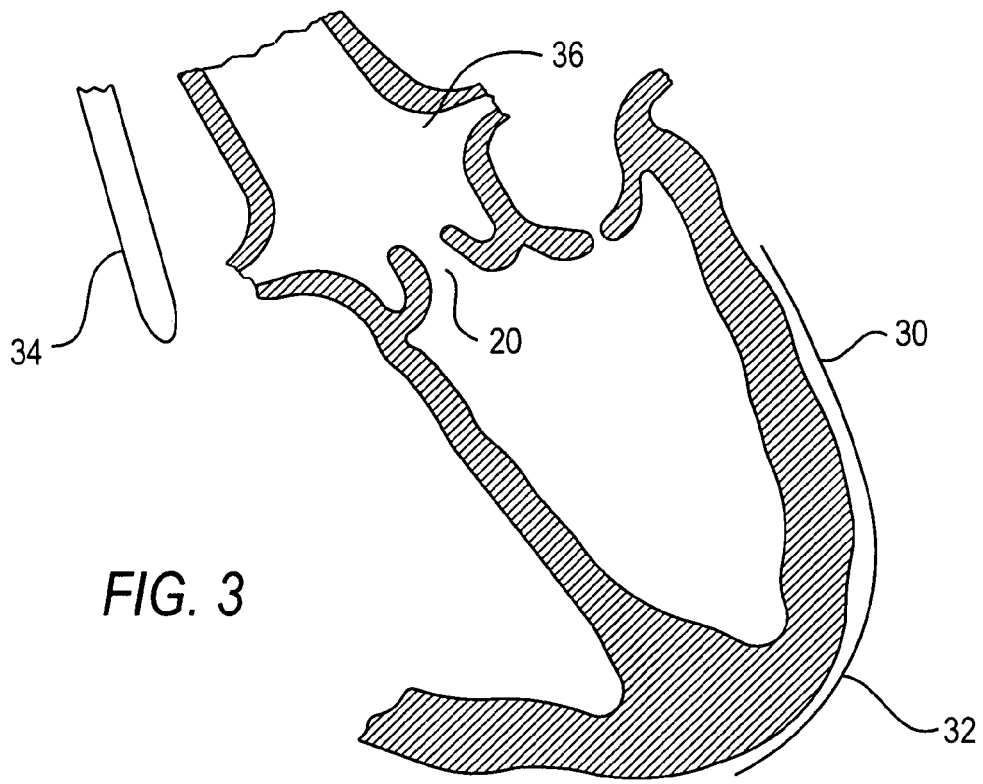
FIG. 3 is a perspective view of an illustrative embodiment of apparatus in accordance with the principles of the present invention.

In addition to the thoracotomy access site, the surgeon may also desire endoluminal (e.g., percutaneous) access sites, preferably via the patient's femoral vein or artery. A femoral vein access site may be used to place ultrasound equipment 34 inside the patient's right atrium adjacent aortic valve 20 and sino-tubular junction 36, as shown in FIG. 3. Ultrasound equipment 34 may, for example, be an AcuNav™ Diagnostic Ultrasound Catheter. Ultrasound equipment 34 could also be placed via the internal jugular vein (IJV). Placement of ultrasound equipment 34 via a femoral or iliac access site versus an IJV site may reverse the orientation of ultrasound equipment 34 (i.e., from which direction ultrasound equipment 34 enters the patient's right atrium). As an alternative to percutaneous ultrasound equipment, a surgeon may choose to use esophageal visualization technology such as, for example, TransEsophageal Echo ("TEE") to provide an image of the target valve replacement site.

Figure 4:
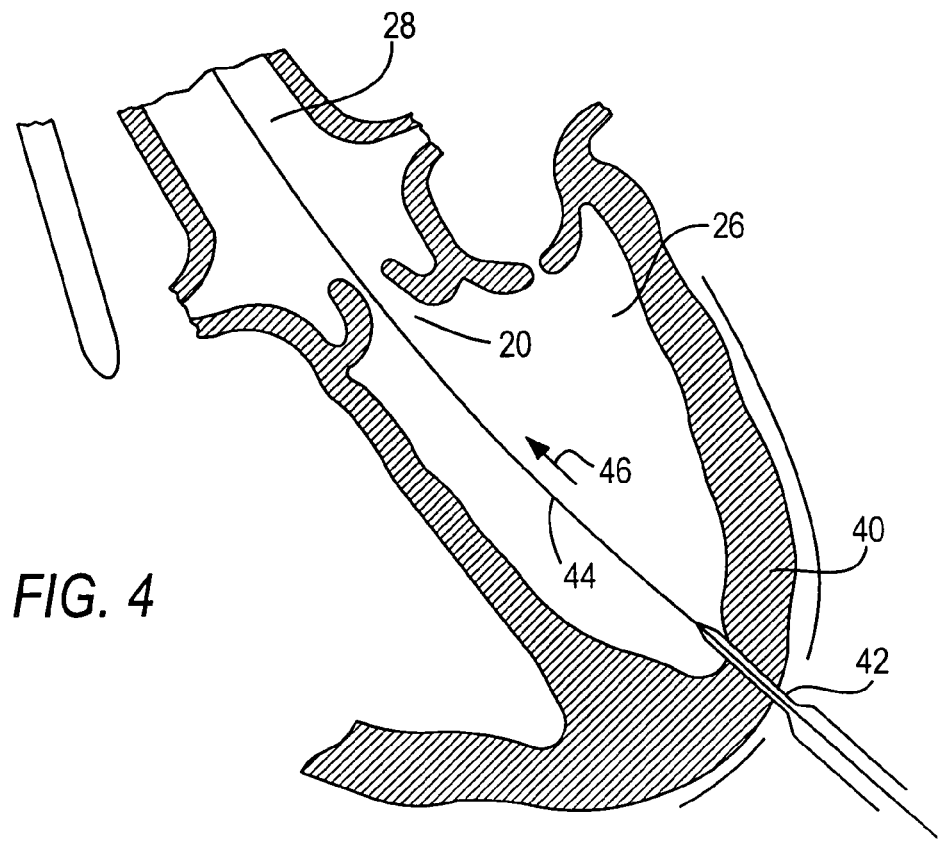
FIG. 4 is a view similar to FIG. 3 showing a later stage in the illustrative procedure depicted in part by FIG. 3, together with related apparatus, all in accordance with this invention.

After accessing the heart muscle via one or more thoracotomies described above, an incision is made to pericardium 30 at access site 32. Next, myocardium 40 is punctured with needle 42 or other suitable device to gain access to the inner heart structures (in this case, left ventricle 26), as illustrated in FIG. 4. Guidewire 44 is fed into left ventricle 26 in antegrade direction 46. Following the direction of blood flow, guidewire 44 is advanced through aortic valve 20 and into aorta 28. Guidewire 44 may be further advanced into the iliac or femoral arteries. In such embodiments, a wire with a snare loop may be advanced from the femoral endoluminal access site to retrieve guidewire 44 and pull it out the femoral endoluminal access site. This enables guidewire 44 to pass through the patient's vasculature from transapical access site 17 to the femoral endoluminal access site.

Figure 5:
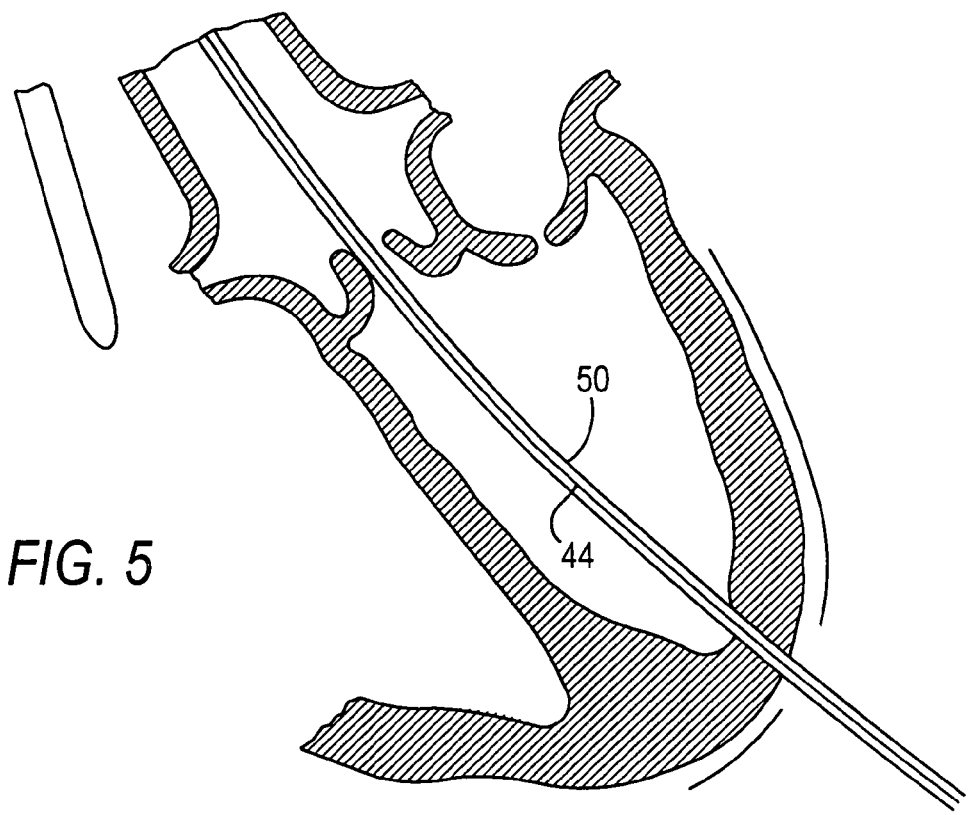
FIG. 5 shows an even later stage in the illustrative procedure depicted in part by FIGS. 3 and 4, together with related apparatus, all in accordance with this invention.

Guidewire 44 may be a relatively thin and flexible guidewire. In order to provide sturdier support for the exchange of surgical tools, it may be desirable to replace guidewire 44 with a stiffer guidewire. This is accomplished by passing catheter 50 over guidewire 44, removing guidewire 44 from the patient while catheter 50 holds its place, and inserting a stiffer guidewire, as shown by FIG. 5. Once the stiffer guidewire has been passed through catheter 50, catheter 50 can be removed, leaving the stiffer guidewire in place. A guidewire that is externalized from the patient at both ends (i.e., at the transapical site and the femoral endoluminal access site) would allow bi-directional use. Wire-guided devices could be inserted from both ends, allowing the insertion of wire-guided devices from the antegrade and retrograde directions.

Figure 19:
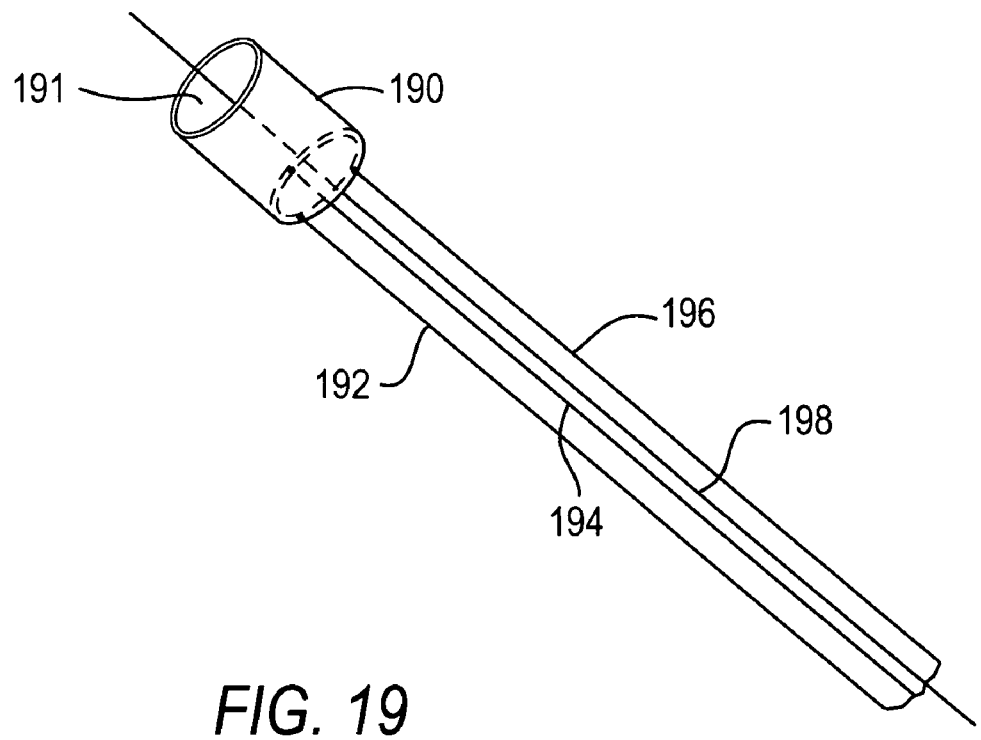
FIG. 19 is a perspective view of an illustrative embodiment of apparatus in accordance with the principles of the present invention.
Figure 19A:
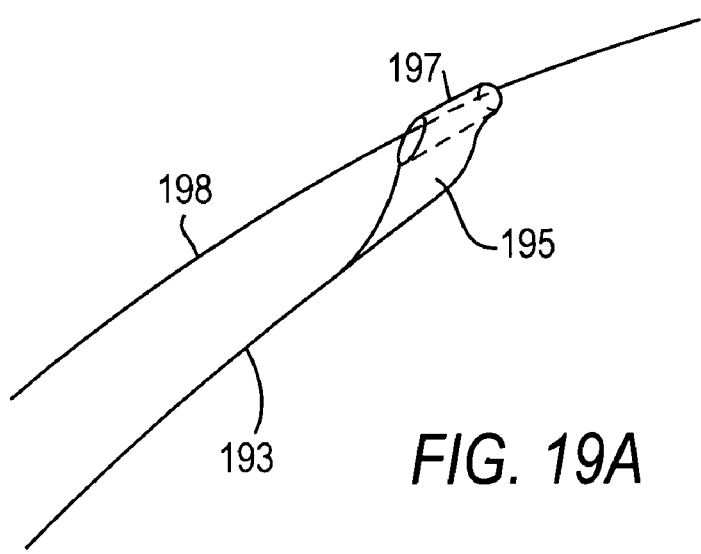
FIG. 19A is a perspective view of an illustrative embodiment of apparatus in accordance with the principles of the present invention.

In some embodiments of the present invention, multiple guidewires may be placed to provide access for more surgical devices. Using multiple guidewires may provide advantages such as allowing two devices to be placed next to each other (e.g., intravascular ultrasound could be operated next to valve deployment devices). Multiple guidewires may be placed simultaneously as shown in FIGS. 19 and 19A. Guidewire 198 is the already placed initial guidewire (e.g., guidewire 66 of FIG. 6). Wire placement device 190 or 195 glides over guidewire 198 via hollow opening 191 or 197. Additional guidewires 192, 194, and 196 are attached to wire placement device 190 such that all three additional wires are placed at one time. Additional guidewire 193 is attached to wire placement device 195. Any number of guidewires can be attached to wire placement device 190 or 195 so that the desired number of additional guidewires can be simultaneously placed. Wire placement device 190 or 195 may be broken-off or cut away from the additional guidewires once they have been placed through the body. Also, wire placement devices 190 and 195 may incorporate locking mechanisms. Thus, if the additional guidewires are not to be passed all the way through the body such that they emerge at a second end, the wires can be clamped in place (e.g., wire placement devices 190 and 195 may clamp to the initially placed guidewire to hold the additional guidewires in place).

Next, a dilator (not shown) may be advanced over stiffer guidewire 66 (FIG. 6) to dilate the opening created by needle 42 (FIG. 4) in myocardium 40. Once the opening in myocardium 40 has been dilated to the necessary size, access device 60 can be placed. Access device 60 will provide an access port to the surgical site inside left ventricle 26, while preventing the heart chamber from bleeding out. Access device 60 (shown in FIG. 6) allows for easy and rapid insertion of tools, devices, instruments, wires, catheters and delivery systems that will enable the repair or resection of a diseased heart valve or the implantation or replacement of a new heart valve.

A second access device or introducer may be placed inside the distal artery (e.g., the femoral artery at the endoluminal access site). Furthermore, additional guidewires may be placed from the endoluminal access site. One or more additional guidewires may be placed using the piggy-back approach described in more detail above.

Access device 60 may include catheter 64 with distal balloon 61 and proximal balloon 62. Balloons 61 and 62 may sandwich myocardium 40 to prevent bleeding from left ventricle 26. Access device 60 may be anchored in other suitable ways, as long as left ventricle 26 is appropriately sealed to prevent bleeding, and such that blood flow through the coronary arteries is not occluded. Access device 60 also includes valve 63. Valve 63 allows the passage of guidewire 66 and the insertion of surgical tools while preventing bleeding through catheter 64. Valve 63 may be mechanically operable as an iris diaphragm (e.g., like the aperture of a lens). Alternatively, valve 63 may be constructed of an elastic material with a small central opening that is dilated by whatever equipment is inserted therethrough, but always maintains a fluid-tight seal with the inserted equipment. Valve 63 may compose any fluid-tight valve structure.

Access device 60 can include one or multiple valve-like structures, like valve 63. Multiple valves in series may act as added protection against leakage from the heart chamber. Furthermore, because of the potential for leakage around multiple tools, access device 60 may include multiple valves in parallel. Thus, each tool could be inserted through its own valve. This could ensure that a proper seal is created around each tool being used during the operation.

Figure 7:
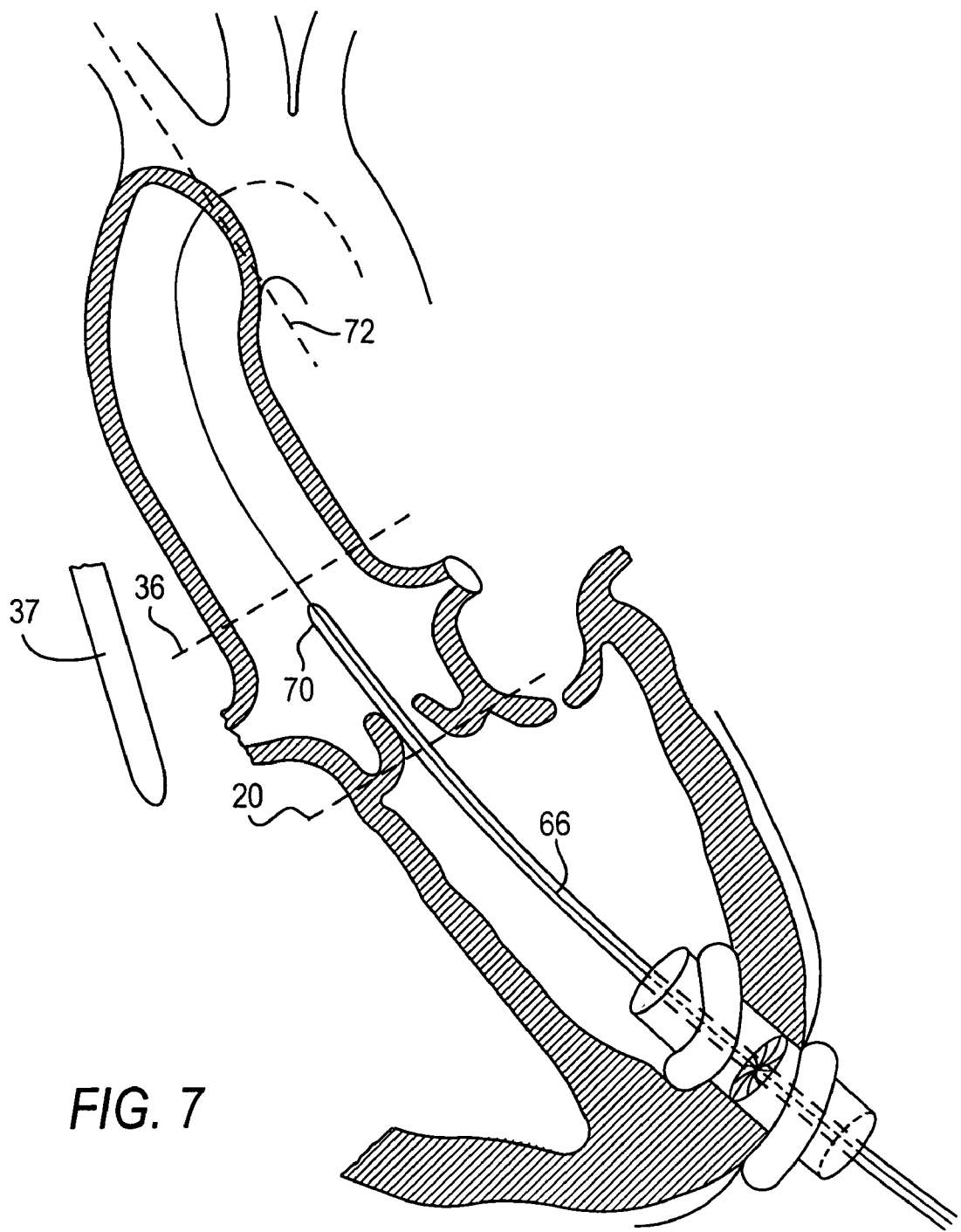
FIG. 7 shows an even later stage in the illustrative procedure depicted in part by FIGS. 3-6, together with related apparatus, all in accordance with this invention.

In some embodiments of the present invention, various endovascular, endocardiac, and/or endoluminal visualization aids may be used. Such devices are illustrated in FIG. 7. Additionally, extracorporeal X-ray based radiographic devices may be employed. Preferably, intracardiac ultrasound 34 is placed in the right atrium via a femoral vein, and intravascular ultrasound (IVUS) 70 is placed over guidewire 66 and into a heart chamber or into the diseased valve. External fluoroscopy is also utilized to map and visualize the surgical site.

IVUS 70 may be used to locate aortic valve 20, sino-tubular junction 36, and brachio-cephalic trunk 72. In order to determine the precise location of each, IVUS probe 70's location is simultaneously tracked with AcuNav™ 34 and fluoroscopy. Once each landmark is located, a radioopaque marker may be placed on the patient's skin or the heart's surface so that extracorporeal fluoroscopy can later be used to relocate these points without IVUS 70 taking up space inside the surgical site. The end of the native leaflet in systole may also be marked with a radioopaque marker in order to temporarily define the target zone. This technique requires that the patient and the fluoroscopy equipment not be moved during the procedure, because landmarks inside the heart and aorta are being marked by radioopaque markers placed on the patient's skin outside the body or on the beating heart's surface. It may be desirable to place the radioopaque markers directly on the heart and aorta.

IVUS 70, AcuNav™ 34, and the fluoroscopy equipment can also be used to take measurements of the diseased valve. This allows the surgeon to chose a properly sized replacement heart valve. As an alternative to fluoroscopy, a surgeon may choose to use standard dye visualization techniques such as angiography. Although it would create material limitations for manufacturing the replacement heart valve, MRI technology could be used as an alternative means of visualizing the target surgical site. Additionally, with the development of cameras that can see through blood, direct optical technology could be used to create an image of the target site. Real-time three-dimensional construction of ultrasound data is another visualization procedure that is currently under development that could provide a suitable alternative.

With respect to direct optical technology, a clear liquid could be introduced to the aorta or other components of the circulatory system near the target surgical site. Placing a clear liquid that is capable of carrying oxygen (i.e., capable of carrying on the blood's biological function, temporarily) in the patient's circulatory system would improve the ability to use direct optical imaging. Furthermore, because the heart is beating, the patient could be transfused with the clear oxygen-carrying fluid for the duration of the procedure so that direct optical visualization is enabled throughout the procedure. The patient's regular blood would be retransfused at the conclusion of the procedure.

Another option for a direct visualization technique includes placing a transparent balloon (filled with a transparent fluid such as water) in front of the camera. The camera and liquid-filled balloon are pushed against the surface that the surgeon wishes to view. The transparent balloon displaces blood from the camera's line of sight such that an image of what the camera sees through the balloon is transmitted to the surgeon.

Figure 8:
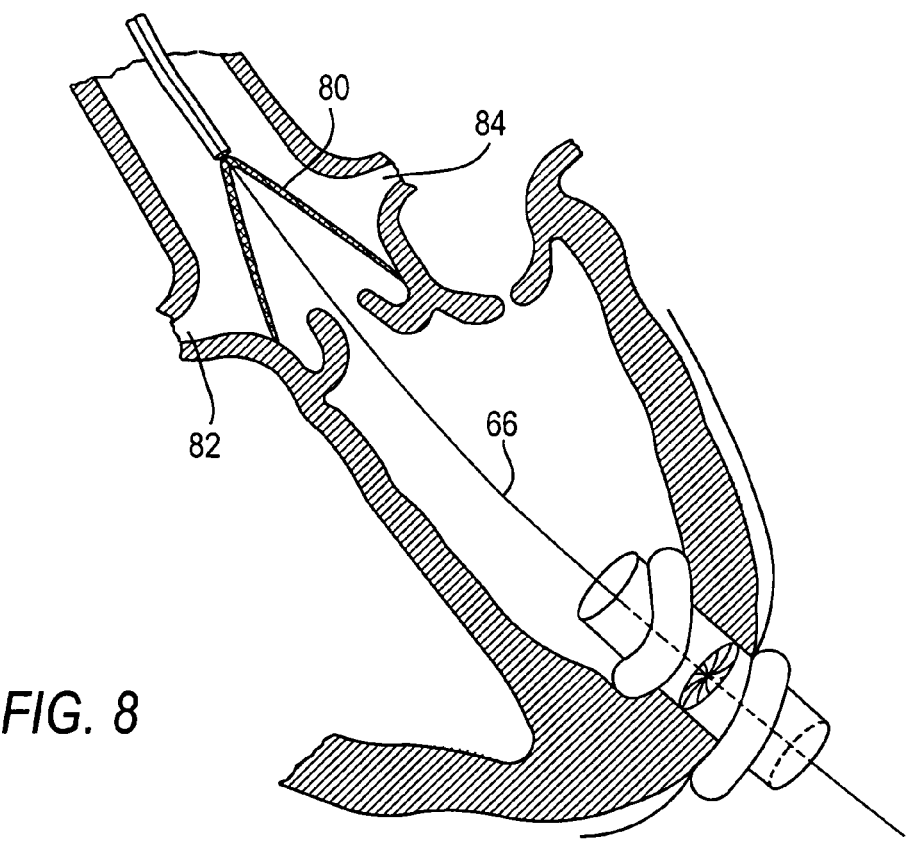
FIG. 8 shows an even later stage in the illustrative procedure depicted in part by FIGS. 3-7, together with related apparatus, all in accordance with this invention.

Furthermore, the invention may include the placement of embolic protection device 80 in the ascending aorta by means of a catheter, as shown in FIG. 8. Embolic protection device 80 is preferably placed from the endoluminal femoral access site in a retrograde approach to the aortic valve site. Embolic protection device 80 may comprise a filtering mesh or net made from any suitable material. The chosen material should be able to be collapsed, expanded, and re-collapsed multiple times. Embolic protection device 80 may alternatively be placed from the antegrade direction. Either approach may be made using guidewire 66 or additional guidewires inserted in accordance with the present invention.

Figure 20:
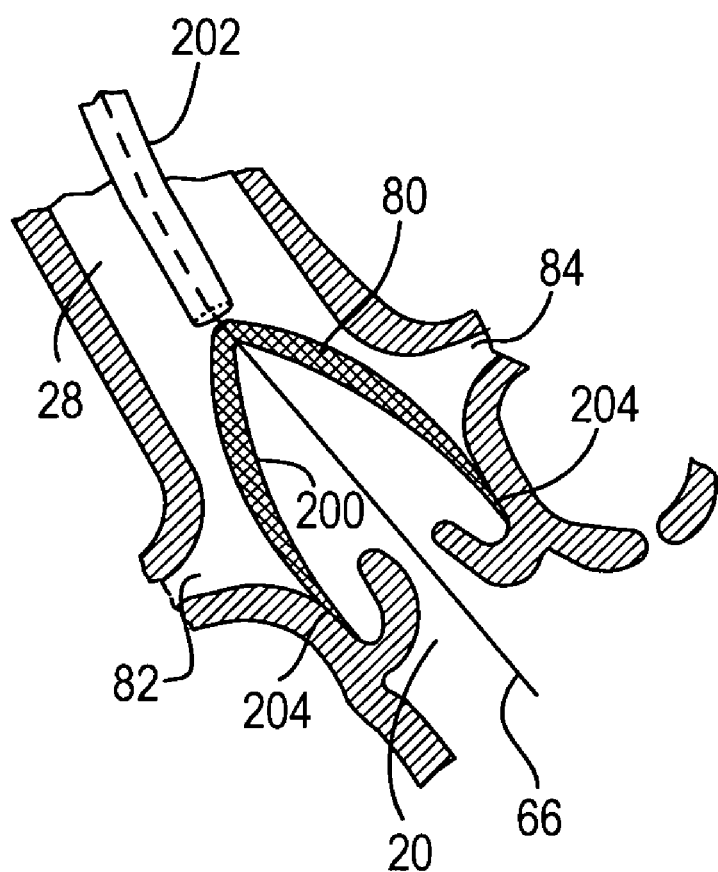
FIG. 20 is a perspective view of an illustrative embodiment of apparatus in accordance with the principles of the present invention.

Single embolic protection device 80 may have unique properties to protect the outflow region of the aortic valve which feeds aorta 28 and coronary sinuses 82 and 84. Device 80 may comprise tight mesh 200 (see FIG. 20) formed in a conical shape. Conical mesh 200 may terminate in perimeter 204 that exerts a radially outward force on the wall of aorta 28. Device 80 is operated via catheter 202 and is dimensioned so that it is capable of filtering the blood supply to the aorta and the coronary arteries.

Figure 9:
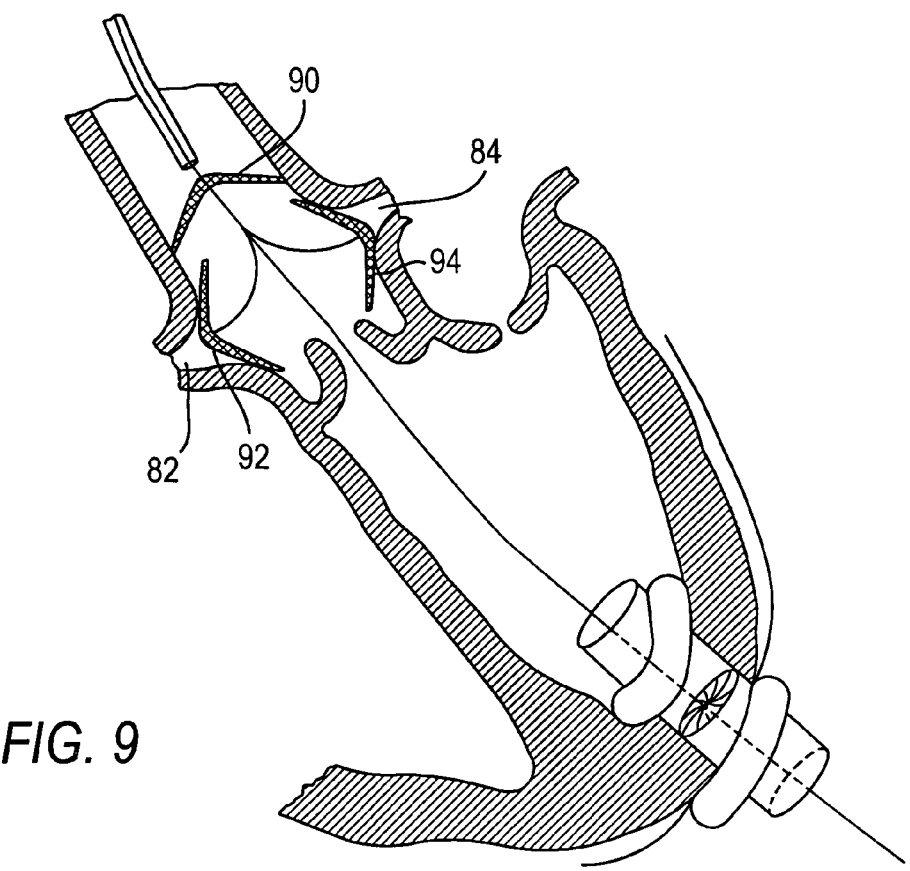
FIG. 9 shows alternative related apparatus to that shown in FIG. 8 and shows an even later stage in the illustrative procedure depicted in part by FIGS. 3-7, together with related apparatus, all in accordance with this invention.

In some embodiments, embolic protection device 80 may be replaced with multiple embolic protection devices 90, 92, and 94, as illustrated in FIG. 9. In FIG. 9, each of coronary sinuses 82 and 84 is protected by its own embolic protection device (embolic protection devices 92 and 94, respectively), and aorta 28 is protected by embolic protection device 90. Embolic protection devices 92 and 94 may be placed further into the coronary arteries to keep the surgical site inside the aorta as clear as possible. Embolic protection device 80 of FIG. 8 is designed so that proper placement of the single protection device will prevent the flow of embolic material into any of aorta 28 and coronary sinuses 82 and 84.

Figure 10:
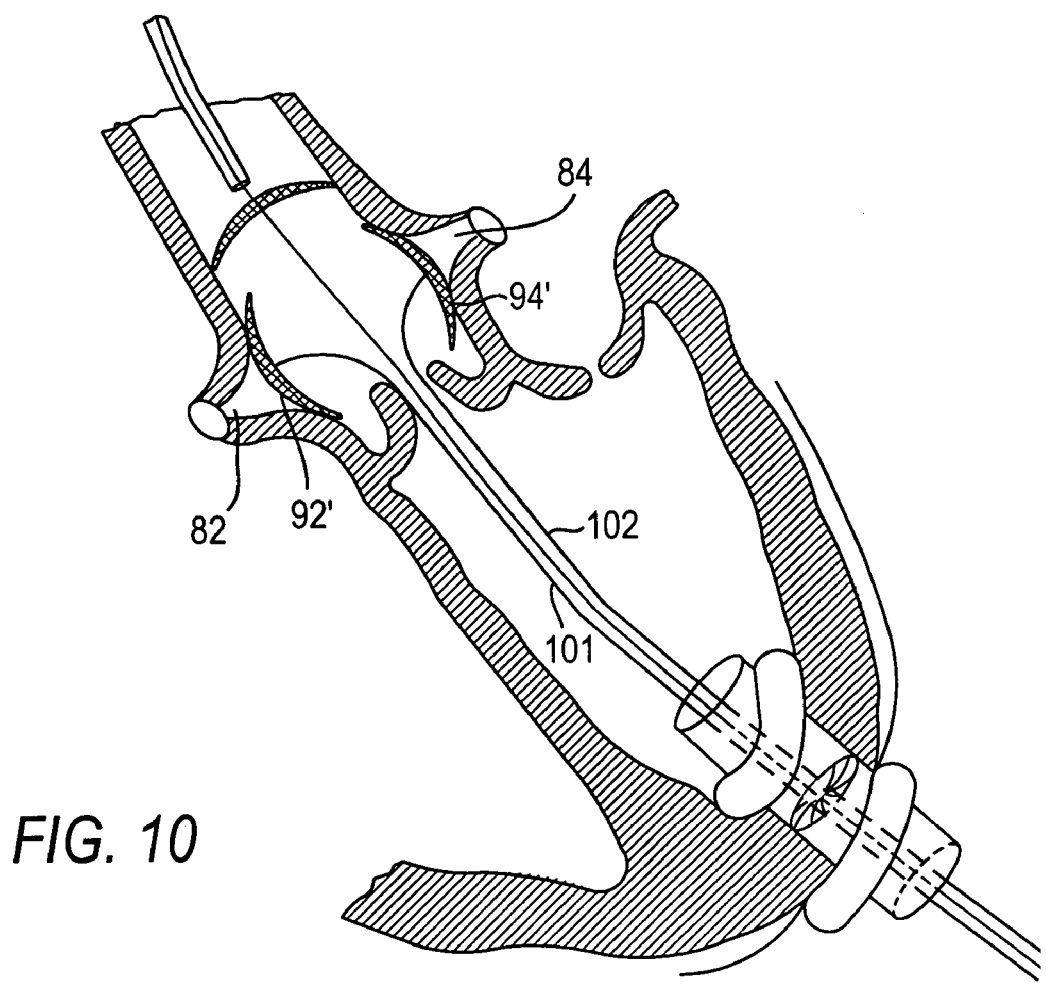
FIG. 10 shows alternative related apparatus to that shown in FIGS. 8 and 9 and shows an even later stage in the illustrative procedure depicted in part by FIGS. 3-7, together with related apparatus, all in accordance with this invention.

In certain embodiments of the present invention, the embolic protection device may be placed in an antegrade approach. For example, FIG. 10 shows embolic protection devices 92' and 94' having been inserted in the antegrade direction. Placing devices 92' and 94' in the coronary sinuses from the antegrade direction leaves guidewires 101 and 102 to exit the patient at the thoracotomy access site. Coronary sinuses 82 and 84 provide useful landmarks in placing a new aortic valve. Thus, by placing devices 92' and 94' in this manner, the surgeon is provided with a guide to proper placement of the new valve (i.e., guidewires 101 and 102 which terminate at coronary sinuses 82 and 84). The new valve may be inserted in the antegrade direction along guidewires 101 and 102 to ensure proper placement.

Additionally, embolic filters may be placed in the brachiocephalic, left common carotid, and left subclavian arteries of the aortic arch.

Some embodiments of the present invention may employ a valve-tipped catheter or other temporary valve device that is capable of temporarily replacing the native valve function during and after resection or removal until the new valve is deployed and functional. Such temporary valve devices may be placed in any number of acceptable locations. For example, when replacing the aortic valve's function, it may be preferable to place the temporary valve in the ascending aorta just distal to the native aortic valve. However, it is possible to temporarily replace the aortic valve function with a device placed in the descending aorta. Such a placement may have the disadvantage of causing the heart to work harder, but such placements have been proven acceptable in previous surgical procedures.

Additionally, some embodiments of the present invention may include the use of a percutaneously placed small caliber blood pump containing an impellor (e.g., a VAD (Ventricular Assist Device)). The VAD may be inserted in a retrograde or in an antegrade direction over guidewire 66. Alternatively, the VAD may be inserted over a secondary guidewire. Because of the resection and implantation equipment that will be inserted in the antegrade direction, it may be desirable to place the VAD in a retrograde approach from the percutaneous femoral access site. The VAD or other temporary pump device will be used to support the heart's natural function while the native valve is being resected or repaired. The temporary assistance device will remain in place until the new valve is deployed and functional.

Figure 39:
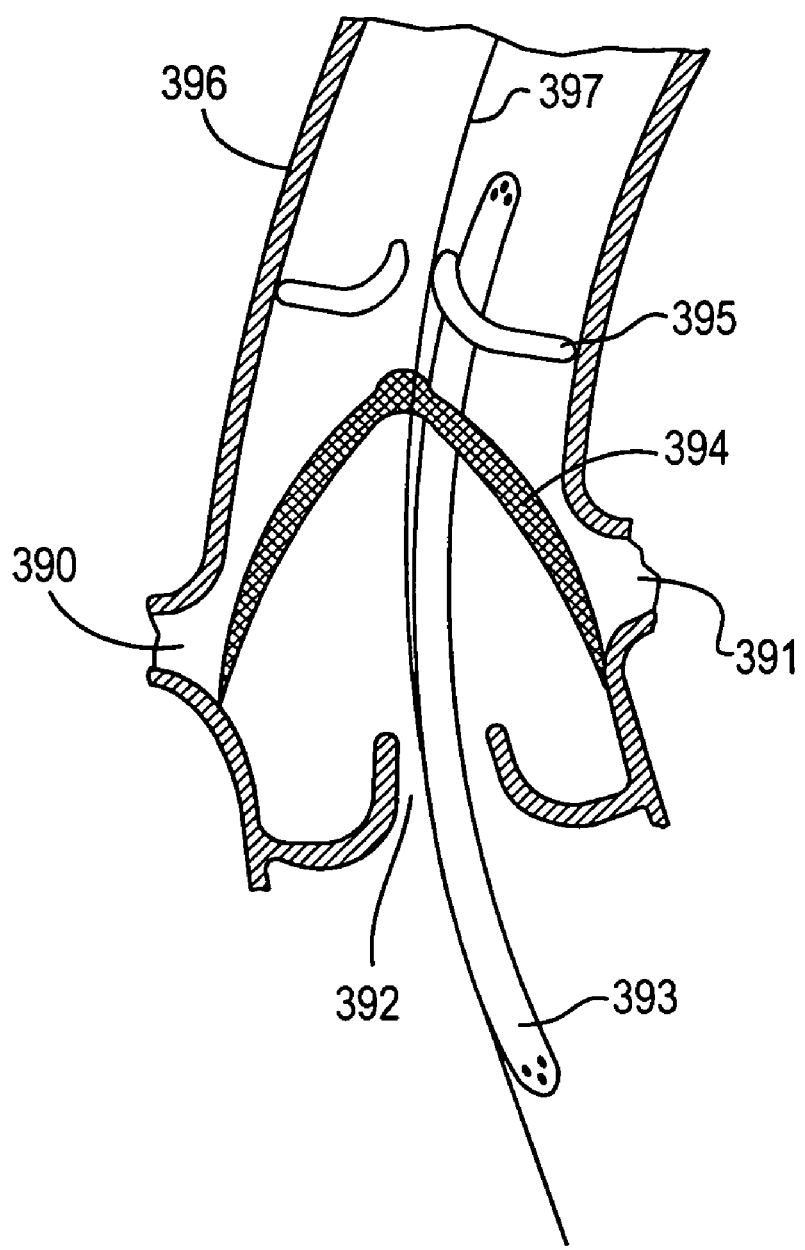
FIG. 39 is a perspective view of an illustrative embodiment of apparatus in accordance with the principles of the present invention.

FIG. 39 shows one possible combination of an embolic filter, temporary valve, and VAD. The FIG. 39 embodiment shows VAD 393 passing through embolic filter 394 and temporary valve 395. These components are positioned distal to aortic valve 392 in ascending aorta 396. Embolic filter 394 is designed to also protect coronary arteries 390 and 391. Embolic filter 394, VAD 393, and temporary valve 395 may all be guided by guidewire 397. This is just one possible arrangement for the components that may be used in a valve repair or replacement procedure.

Figure 11:
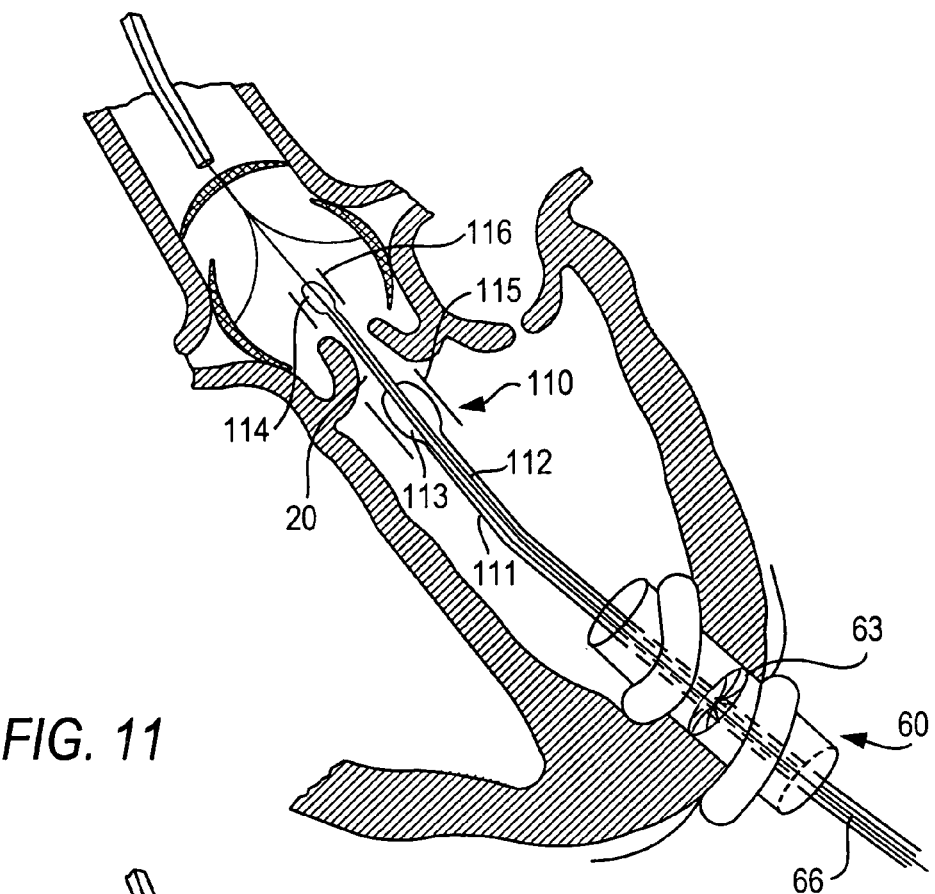
FIG. 11 shows an even later stage in the illustrative procedure depicted in part by FIGS. 3-10, together with related apparatus, all in accordance with this invention.

In some embodiments of the present invention, the placement of a new valve may first involve the full or partial resection of the diseased valve or cardiac structure. To perform a resection of the diseased valve, a surgeon may use valve removal tool 110, shown in FIG. 11. Valve removal tool 110 incorporates outer inflation lumen 111 and inner inflation lumen 112, which is placed coaxially within outer inflation lumen 111. Outer inflation lumen 111 terminates at proximal balloon 113. Inner inflation lumen 112 terminates at distal balloon 114. Coaxial catheters 111 and 112 can be advanced over guidewire 66 and passed through valve 63 of access device 60. Radially expandable proximal cutting device 115 is mounted to the surface of distal balloon 113. Radially expandable distal cutting device 116 is mounted to the surface of distal balloon 114. Valve removal tool 110 is advanced with balloons 113 and 114 in the deflated state and cutting devices 115 and 116 in the collapsed state until distal cutting device 116 is located just distal to diseased aortic valve 20 and proximal cutting device 115 is positioned just proximal to diseased aortic valve 20.

Figure 12:
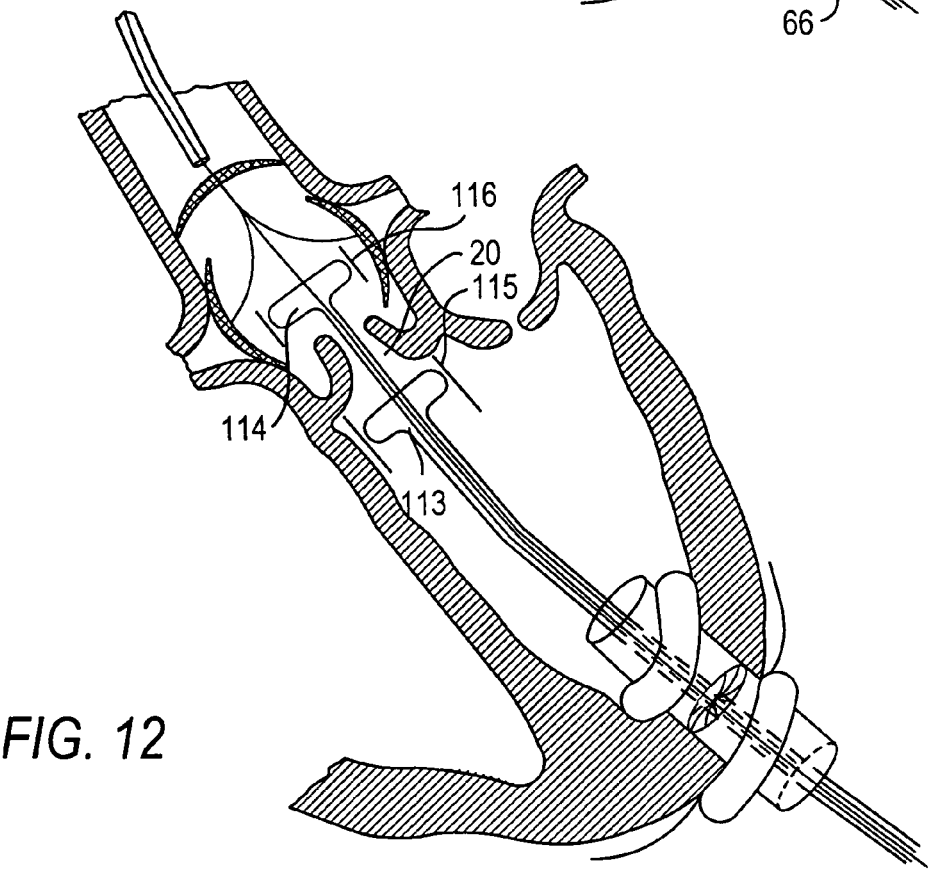
FIG. 12 shows an even later stage in the illustrative procedure depicted in part by FIGS. 3-11, together with related apparatus, all in accordance with this invention.
Figure 13:
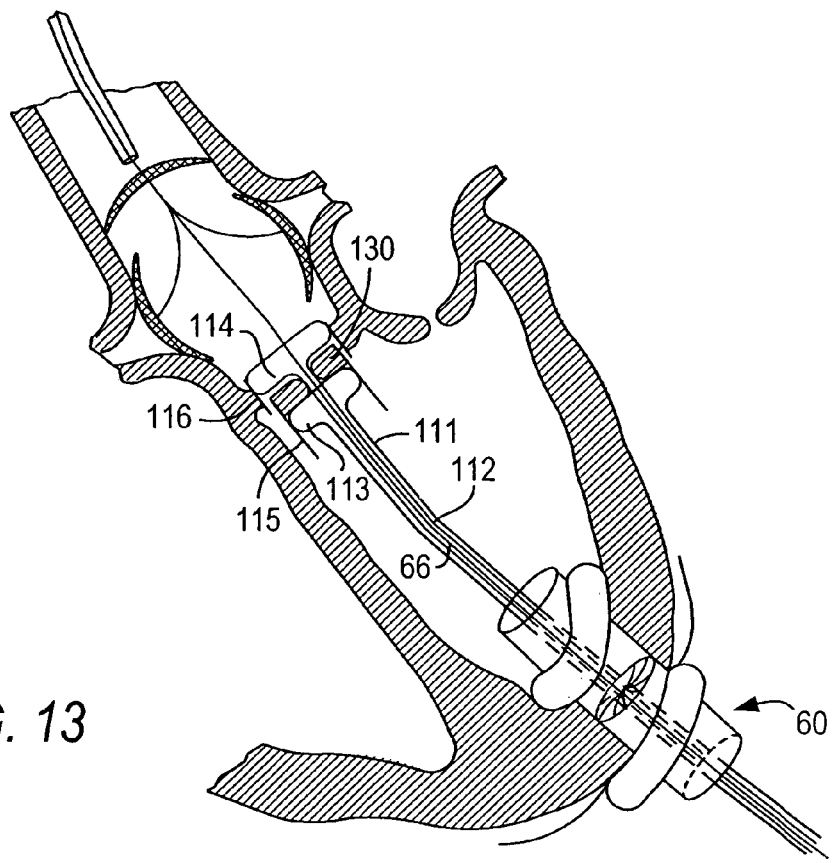
FIG. 13 shows an even later stage in the illustrative procedure depicted in part by FIGS. 3-12, together with related apparatus, all in accordance with this invention.

As shown in FIG. 12, balloons 113 and 114 are inflated such that cutting devices 115 and 116 are radially expanded to the approximate diameter of the diseased valve. Next, inner inflation lumen 112, distal balloon 114, and distal cutting device 116 are pulled in the retrograde direction. This causes cutting devices 115 and 116 to cooperate with one another to cut away diseased aortic valve leaflets 130, as shown in FIG. 13. Balloons 113 and 114 can be deflated and cutting devices 115 and 116 collapsed while retaining cut away valve leaflets 130. Thus, valve removal tool 110 and resected leaflets 130 can be removed via access device 60.

Further, valve removal device 110 may possess self-centering properties. Valve removal device 110's cutting mechanism may allow the device to cut or resect any calcified or diseased tissue within the heart cavities or the vasculature. The size or cut of each bite made by the removal device, as well as the shape of the cut may be determined by the surgeon by adjusting the valve removal device.

When performing surgical techniques inside a patient's vasculature, it may be beneficial to use ring-shaped balloons so that blood can continue to circulate through the balloon. Also, whether using ring-shaped balloons or more standardized balloons, it may be beneficial to use a balloon that has more than one chamber, so that the balloon can be selectively inflated. Examples of a ring-shaped balloon and a cylindrical balloon, both having more than one inflation chamber are illustrated in FIGS. 37 and 38, respectively.

Figure 37:
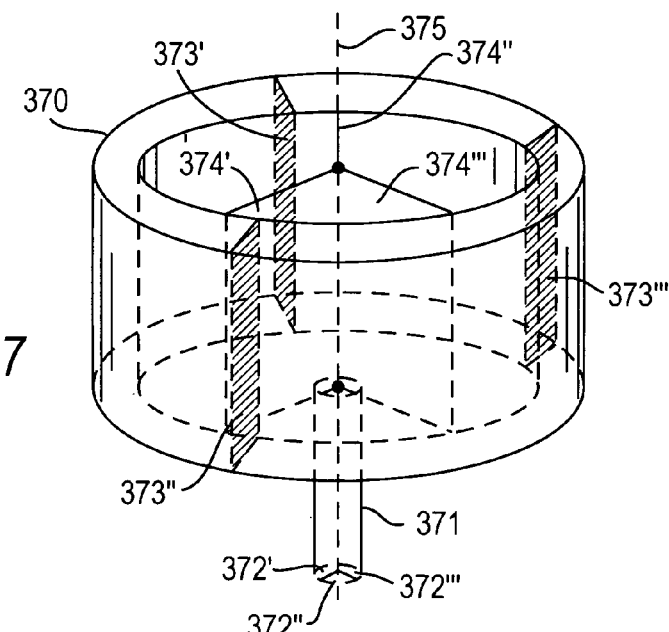
FIG. 37 is a perspective view of an illustrative embodiment of apparatus in accordance with the principles of the present invention.

FIG. 37 shows ring-shaped balloon 370. Balloon 370 may be divided into three inflation chambers by dividers 373', 373", and 373'". Each inflation chamber may be attached to an inflation flange (e.g., flanges 374', 374", and 374'"). Each inflation flange is correspondingly attached to an inflation lumen of catheter 371 (e.g., inflation lumens 372', 372", and 372'"). Thus, blood flow is able to continue through the three openings left between inflation flanges 374', 374", and 374'". Furthermore, surgical tools (e.g., VADs, etc.) may be passed through the openings. Balloon 370 may be guided by guidewire 375.

Figure 38:
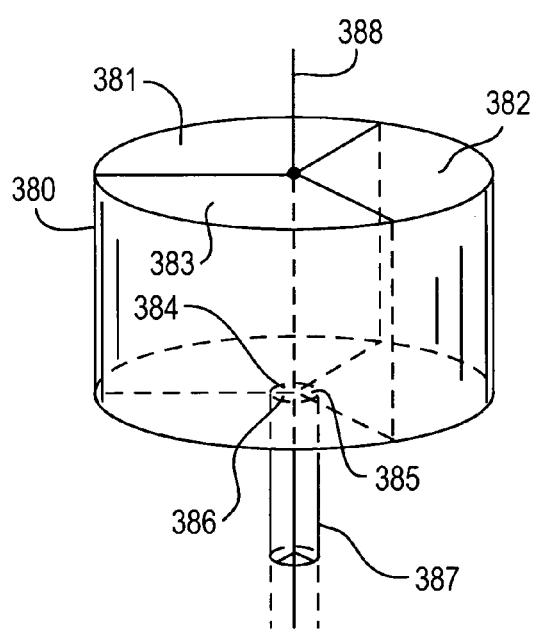
FIG. 38 is a perspective view of an illustrative embodiment of apparatus in accordance with the principles of the present invention.

FIG. 38 shows cylindrical balloon 380 with inflation chambers 381, 382, and 383. The inflation chambers may be selectively inflated by inflation lumens 384, 385, and 386, respectively of catheter 387. Balloon 380 may be guided by guidewire 388. By providing selectively inflatable chambers in either type of balloon, a surgeon may have the ability to manipulate tissue inside a patient's vasculature or properly position surgical equipment and prostheses, for example.

Figure 21:
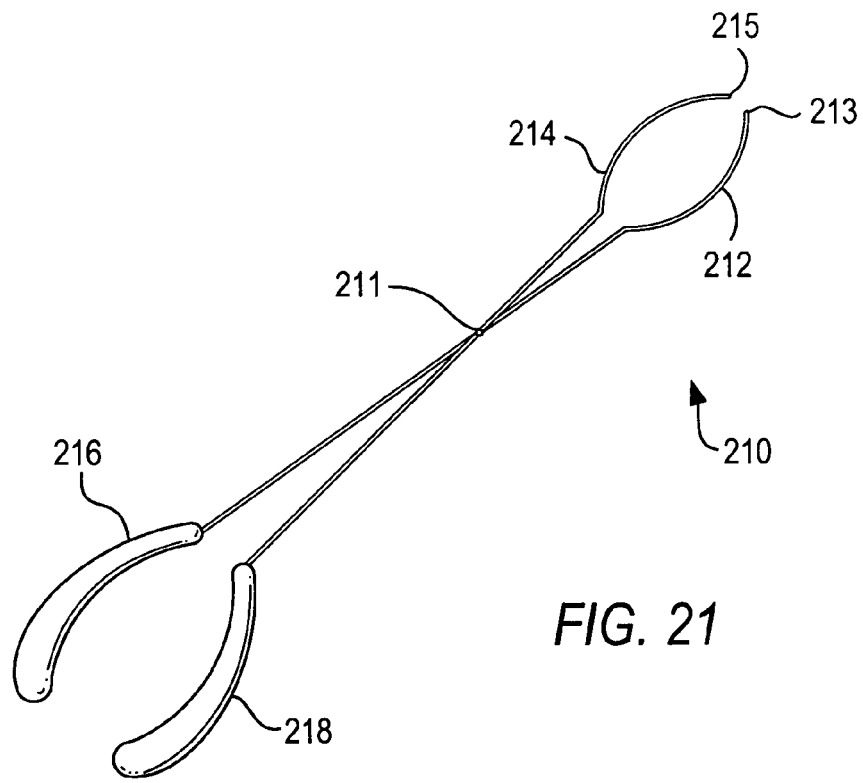
FIG. 21 is a perspective view of an illustrative embodiment of apparatus in accordance with the principles of the present invention.

In some embodiments of the present invention, a valve removal tool such as ronjeur device 210 may be used (see FIG. 21). Ronjeur device 210 may have spoon-shaped heads 212 and 214 which are operably controlled by handles 216 and 218 via hinge 211. Spoon-shaped heads 212 and 214 may have sharpened tips 213 and 215, respectively. Ronjeur device 210 may be used to bite away the leaflets of a diseased valve and trap the dissected tissue within spoon-shaped heads 212 and 214. Ronjeur device 210 may be operable via access device 60.

Figure 22:
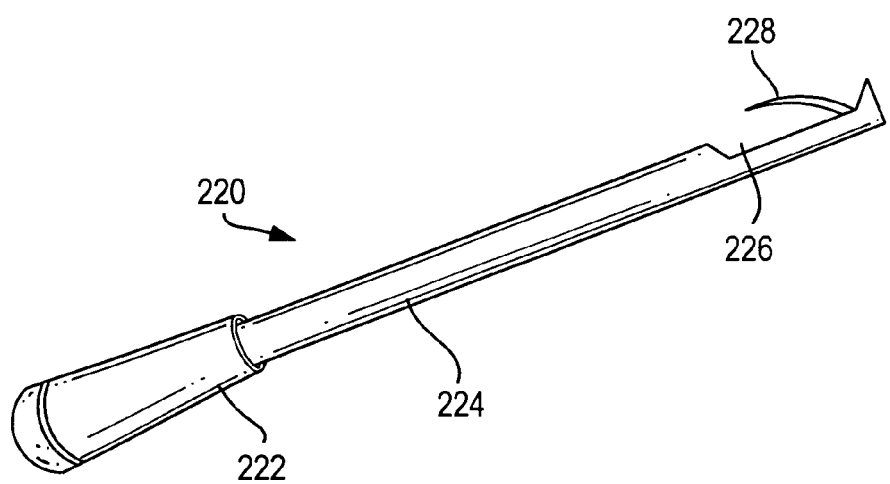
FIG. 22 is a perspective view of an illustrative embodiment of apparatus in accordance with the principles of the present invention.

In other embodiments of the present invention, valve resector 220 of FIG. 22 can be used to resect the diseased valve. Valve resector 220 has handle 222, shaft 224, recess 226, and resector tip 228. Resector tip 228 may be used to cut away or tear away the diseased leaflets of a native valve. Recess 226 may be used to retain the resected tissue for removal. Resector tip 228 may also be mechanically operable to snip away the diseased leaflets. Resector 220 is also operable via access device 60. Other suitable techniques for resecting a diseased valve may also be used before implanting a new valve.

In preparation for valve resection, it may be beneficial to soften or break-up the calcification of the diseased valve. Concentrated ultrasound waves could be used to break-up the valve's calcification. A similar procedure is used to break down kidney stones in some patients. Calcification of the aortic valve is often trapped in tissue pockets. Thus the broken-down calcification would likely be retained by the valve leaflets. However, the leaflets would now be more pliable and easier to compress behind a new valve or to remove. An intraluminal ultrasound device may be used to deliver the concentrated ultrasound waves. Furthermore, an intraluminal reflector may be used to magnify the waves' intensity and break-up the calcium deposits even quicker.

In addition to or as an alternative to resecting the diseased valve, plaque or calcification of a diseased valve may be chemically dissolved. With embolic protection devices 90, 92, and 94 in place, a chemical can be introduced to the diseased valve that will dissolve or release the plaque deposits. The target valve site may first be isolated to contain the chemical during this process. This isolation may be achieved by inflating two balloons to create a chemical ablation chamber defined by the wall of the aorta and the two balloons.

Figure 36:
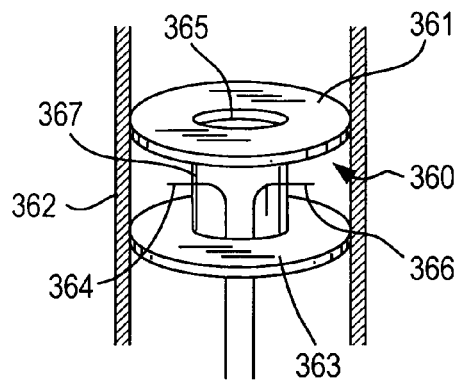
FIG. 36 is a perspective view of an illustrative embodiment of apparatus in accordance with the principles of the present invention.

Isolation may also be achieved by a device like ablation chamber 360 shown in FIG. 36. Ablation chamber 360 is positioned inside the patient's vasculature (e.g., aorta 362). The chamber may be placed percutaneously, by direct access, or by any other suitable technique. Ablation chamber 360 comprises ring-shaped balloons 361 and 363. Balloons 361 and 363 are joined by tubular member 367 which creates a channel for blood to by-pass the ablation site. A ventricular assist device may be inserted through opening 365 in tubular member 367 to aid the patient's blood flow through the temporarily narrowed passageway. Ablation chamber 360 may include chemical introducer 364 and chemical evacuator 366 to introduce a chemical to the ablation site and to clear the chemical from the ablation site when the procedure is completed. Thus, the chemical ablation procedure is performed in the chamber of the isolated segment of the aorta while normal circulatory function takes place. Such a technique isolates the chemical being used from entering the patient's circulatory system. This treatment may be performed to repair a diseased valve, to decalcify a diseased valve before resection by a valve removal tool, or to decalcify a diseased valve before placing a new valve within and over top of the diseased valve. Laser ablation may also be used to break up valve calcification or to remove and destroy diseased valve leaflets.

As another alternative, the diseased and calcified valve can be left as is and a new valve can be implanted within and over top of the diseased valve. In some embodiments of the present invention, it may be desirable to perform a valvuloplasty to percutaneously destroy the leaflets of the diseased valve. It may be easier to dilate the diseased valve with the new valve if it has been partially destroyed first.

Figure 14:
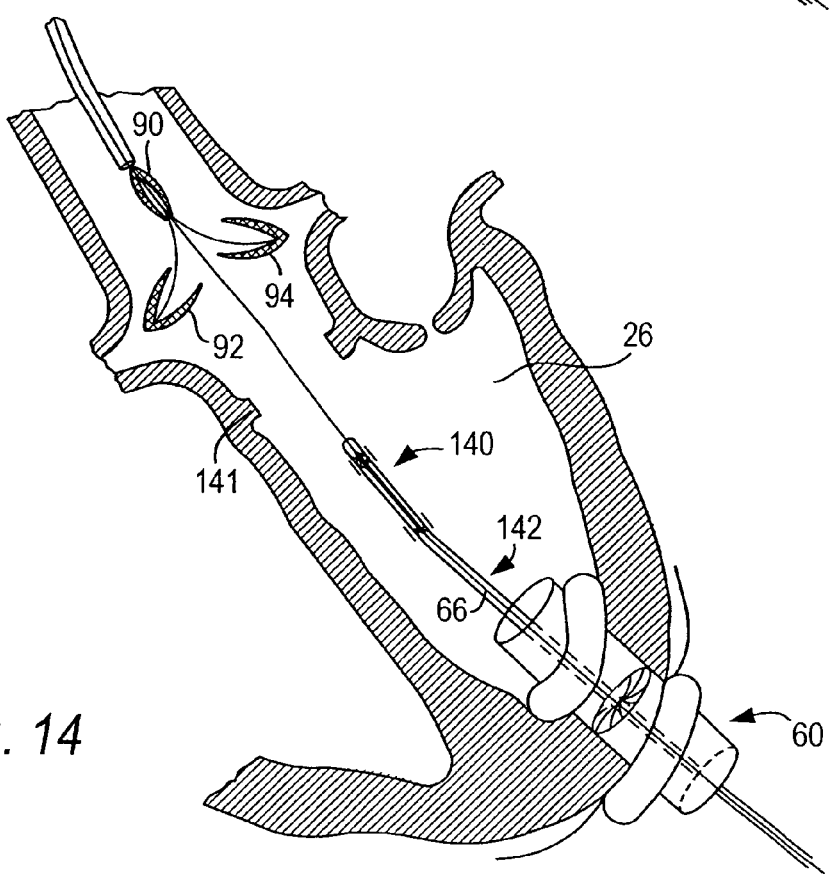
FIG. 14 shows an even later stage in the illustrative procedure depicted in part by FIGS. 3-13, together with related apparatus, all in accordance with this invention.

Once any manipulation of the diseased valve is complete (e.g., marking landmark locations, resecting the diseased leaflets, chemically dissolving calcification, etc.), embolic protection devices 90, 92, and 94 can be removed (FIG. 14). The resection of diseased leaflets 130 (FIG. 13) may leave behind valve rim 141 (FIG. 14). Once the embolic protection devices have been removed, valve delivery device 142 may be inserted into left ventricle 26 via access device 60. Valve delivery device 142 carries new valve 140 in a radially compressed state. Valve 140 has been crimped onto delivery device 142. Alternatively, valve 140 may be folded or collapsed in any other suitable manner. Valve delivery device 142 is advanced along guidewire 66.

In embodiments like that shown in FIG. 10, valve delivery device 142 may also be guided by guidewires 101 and 102 to ensure safe orientation of valve 140 prior to release and deployment. Such a delivery approach would eliminate the danger of coronary obstruction, because guidewires 101 and 102 terminate at coronary sinuses 82 and 84. The spaces between the commissure supports of valve 140 could be properly aligned with coronary sinuses 82 and 84 to allow maximum blood flow to the coronary arteries.

In other embodiments of the present invention, the placement of valve 140 may be assisted by intracardiac ultrasound (i.e., ultrasound equipment 34 of FIG. 7) and fluoroscopy. Positioning, release, and deployment of valve 140 could be simultaneously monitored by the intracardiac ultrasound and fluoroscopy equipment. The fluoroscopy equipment would monitor the target zone based on the radioopaque markers that were placed earlier in the procedure. When the fluoroscopic (marker position) and sonographic (intracardiac ultrasound) target sites are congruent, the proper position for valve deployment has been located. At that moment, valve 140 may be deployed as described below.

Additionally, valve delivery device 142 may contain two radioopaque markers. With the coronaries being visualized with fluoroscopy, the surgeon could visualize the alignment of the two marker bands on delivery device 142. Thus, the surgeon would be able to properly orient the valve such that the commissure posts are properly positioned upon valve deployment.

Figure 15:
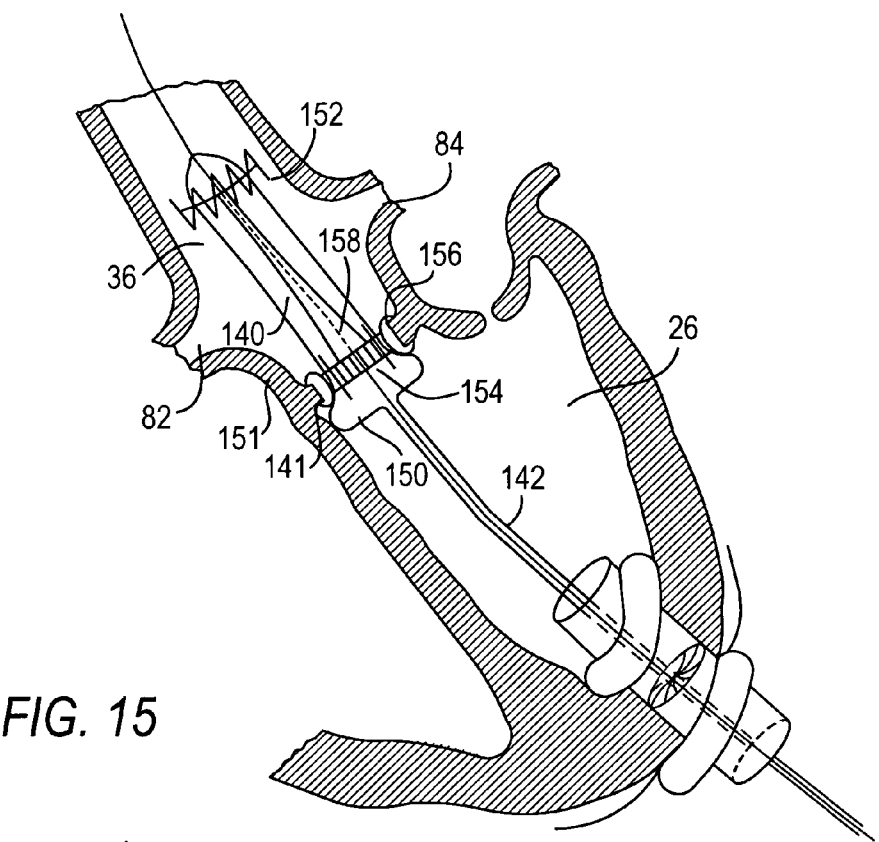
FIG. 15 shows an even later stage in the illustrative procedure depicted in part by FIGS. 3-14, together with related apparatus, all in accordance with this invention.

Valve delivery device 142 may terminate in two phase balloon 150, as shown in FIG. 15. Alternatively, the end of device 142 carrying valve 140 may have two separately operable balloons. The first phase of balloon 150 may be inflated to provide a positioning guide for valve 140. The first phase of balloon 150 provides a bumper such that delivery device 142 is prevented from further advancement when the proximal end of balloon 150 (i.e., the first phase of balloon 150) reaches the region of left ventricle 26 just proximal to the aortic valve site.

Continued expansion of balloon 150 causes base ring 154 of valve 140 to expand. As base ring 154 expands, hooks 156 may bite into remaining aortic rim 141. Alternatively, hooks 156 may not penetrate rim 141, but rather grasp the rim tightly. Commissure support tissue 158 also begins to open up. In some embodiments of the present invention, valve 140 includes distal stent-like structure 152 to support a replacement aortic valve distal to coronary sinuses 82 and 84 in sino-tubular junction 36.

Figure 16:
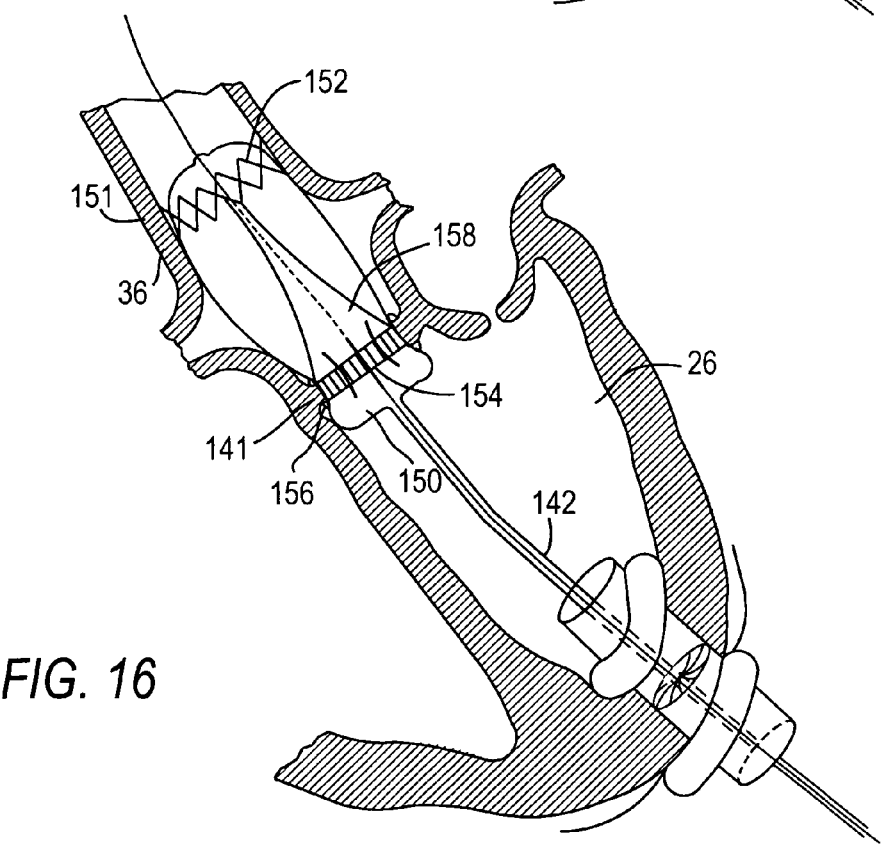
FIG. 16 shows an even later stage in the illustrative procedure depicted in part by FIGS. 3-15, together with related apparatus, all in accordance with this invention.

During expansion, intracardiac ultrasound and fluoroscopy can be used to monitor the orientation and placement of valve 140. Before valve 140 is fully expanded, the surgeon may rotate delivery device 142 such that the spaces between commissure supports 158 align with coronary sinuses 82 and 84. Upon full expansion of ring 154 (see FIG. 16), hooks 156 may fully engage rim 141, and hooks 156 and rim 141 may be partially embedded in aortic wall 151. Stent-like structure 152 may engage aortic wall 151 in sino-tubular junction region 36. Commissure supports 158 will be fully expanded, too. Support structure 152 may expand in unison with base ring 154. Alternatively, valve placement may take place in a stepped process, wherein base ring 154 expands and secures the base of the valve before support-structure 152 expands to secure the distal end of the valve. The location and function of new valve 140 are identified and monitored with IVUS, intracardiac ultrasound, and/or fluoroscopy. Once placement and function is satisfactory to the surgeon, balloon 150 is deflated, and valve delivery device 142 is removed from left ventricle 26.

The implantation process should be done quickly, because there will be a brief total occlusion of the aorta. It may be desirable to block the inflow to the heart. Thus, the heart is not straining to pump blood out, and a dangerous lowering of the patient's heart rate may be prevented.

Valve delivery device 142 may be designed to draw the native leaflets downward when a new valve is being implanted over top of an existing diseased valve. The native leaflets could obstruct blood flow to the coronary arteries. However, pulling the native leaflets downward before compressing them against the aorta wall would prevent such occlusion.

In some embodiments of the present invention, new valve 140 may be a self-expanding valve that can be implanted without the use of a balloon. Base ring 154, hooks 156, and stent-like structure 152 may be constructed of nitinol or some other shape-memory or self-expanding material. In some embodiments, valve 140 may be deployed by mechanical means, such as by releasing a lasso that surrounds the exterior of valve 140 or by operating a mechanical expansion device within valve 140.

In certain embodiments of the present invention, valve 140 may not have a stent-like support structure at the distal end (i.e., stent-like structure 152). If commissure supports 158 are constructed from or supported by a stiff enough support post, valve 140 may not be fixed to the aorta at its distal end. The mounting at base ring 154 may sufficiently secure valve 140 in place to function normally and not obstruct blood flow to the coronary arteries.

Valve 140 may be secured in place by any suitable method for anchoring tissue within the body. The radial expansion forces of base ring 154 may be strong enough to secure valve 140 against dislodgment by radial strength alone. If no native valve rim remains, hooks 156 may be designed to grasp aortic wall 151. Mechanically placed sutures or staples could be used to secure valve 140 in place. Furthermore, biocompatible glue could be used to secure valve 140 in the appropriate position.

Figure 23:
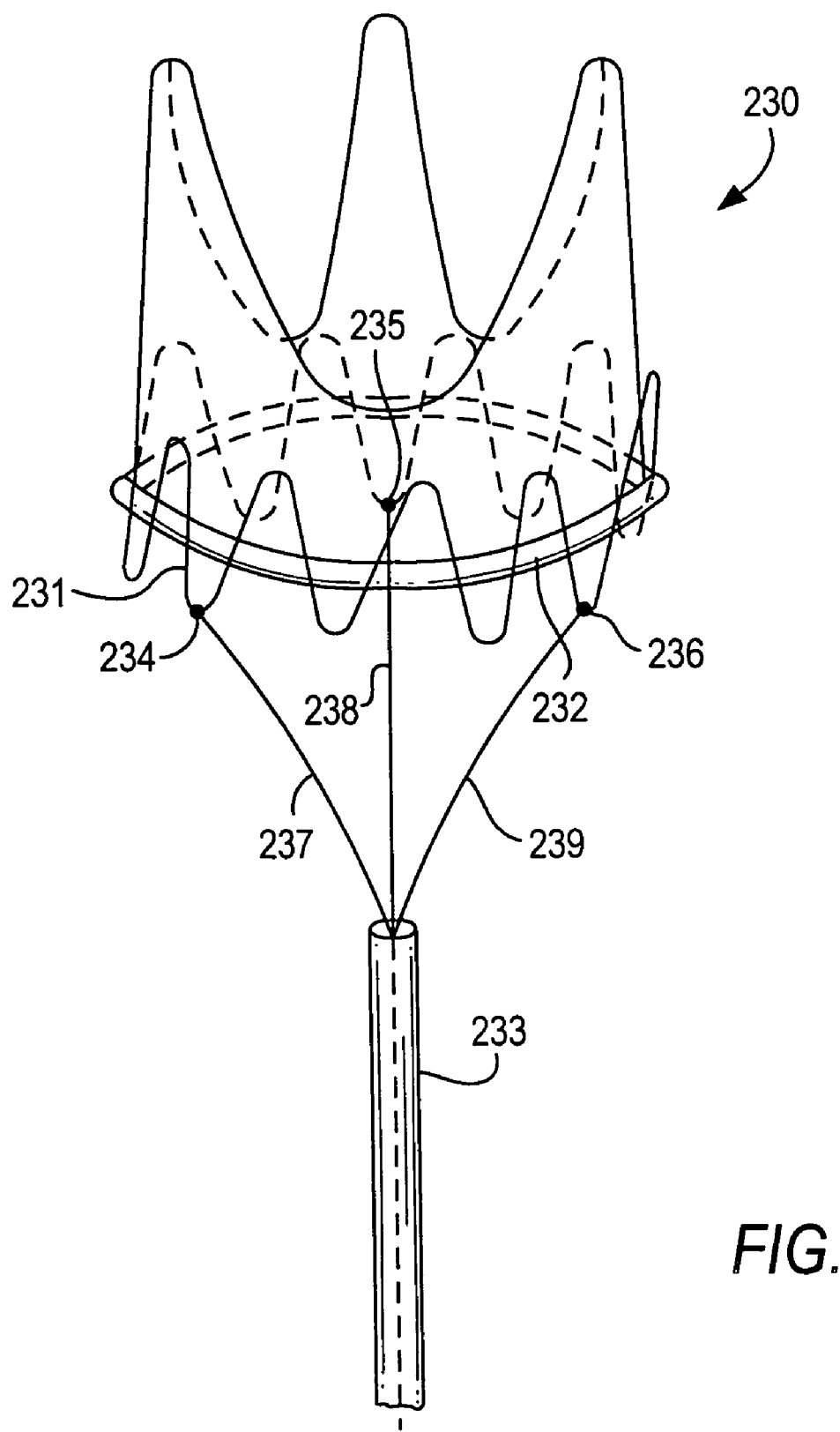
FIG. 23 is a perspective view of an illustrative embodiment of apparatus in accordance with the principles of the present invention.

During a valve implantation procedure, it may be desirable to have the ability to retract expansion of new valve 140. If the commissures are not properly aligned with the coronary arteries or if the valve is not properly positioned within the native annulus, retracting the expansion would enable repositioning or realignment of the valve. Such a retraction technique is illustrated in FIG. 23 wherein valve 230 is one illustration of a possible embodiment of valve 140.

Valve 230 has radially expandable support ring 232 and radially expandable mounting structure 231. Mounting structure 231 may be a sinusoidal ring of nitinol wire. Mounting structure 231 is attached to wires 237, 238, and 239 at points 234, 235, and 236, respectively. By advancing tube 233 or withdrawing wires 237, 238, and 239, mounting structure 231 may be drawn radially inward, effectively retracting the expansion of valve 230. Other means of retracting valve expansion could be employed in accordance with the principles of the present invention.

In some embodiments of the present invention, the dilated opening in myocardium 40 is sealed with an automatic closure device. The automatic closure device may be part of access device 60. Alternatively, the automatic closure device may be inserted through access device 60 such that removal of access device 60 leaves the automatic closure device behind.

Figure 17:
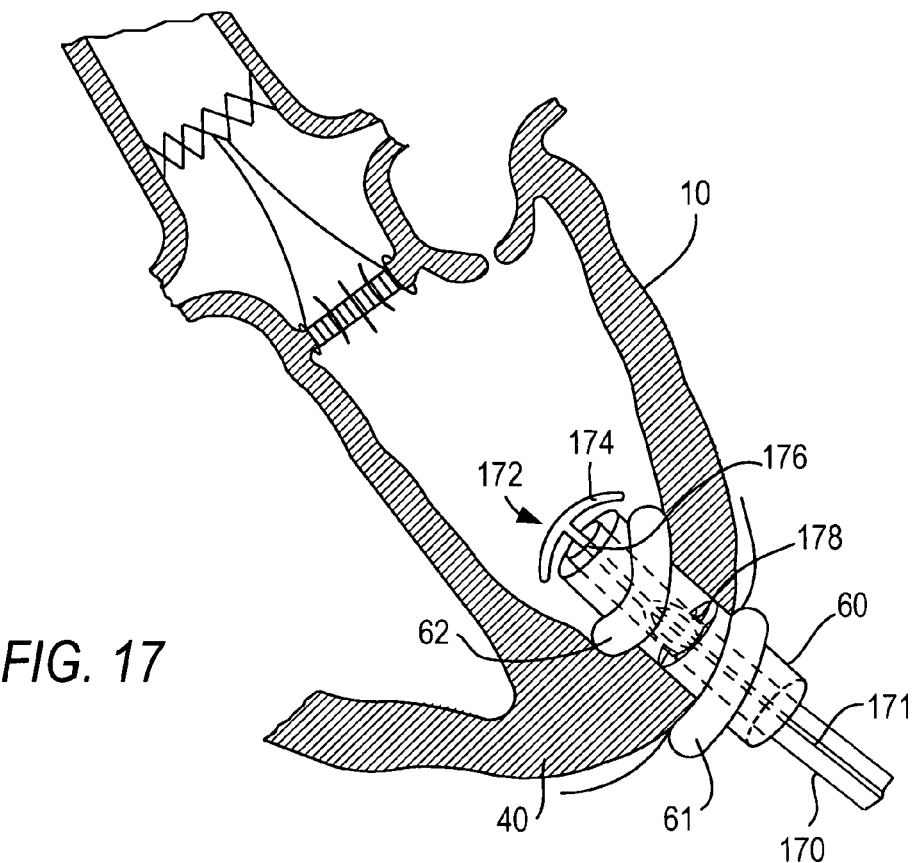
FIG. 17 shows an even later stage in the illustrative procedure depicted in part by FIGS. 3-16, together with related apparatus, all in accordance with this invention.
Figure 18:
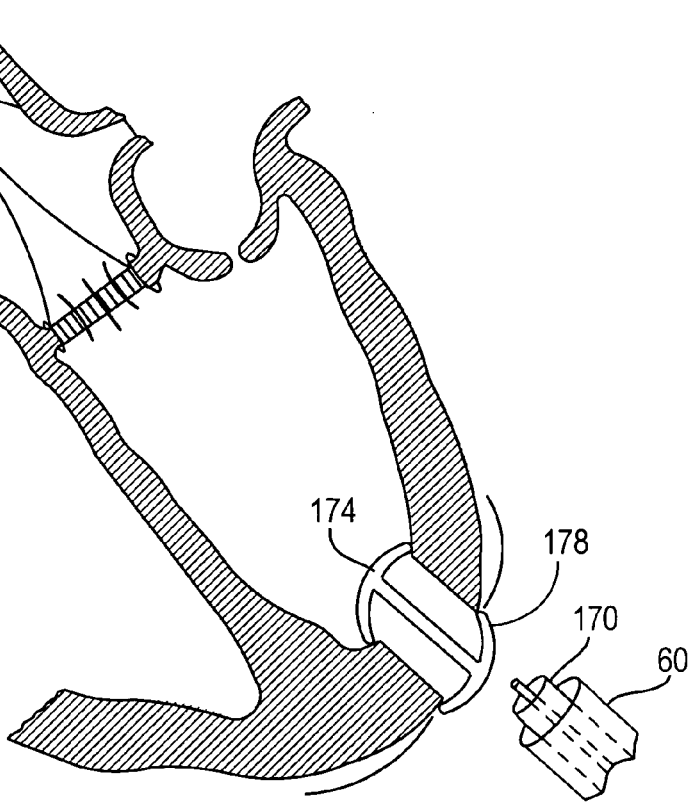
FIG. 18 shows an even later stage in the illustrative procedure depicted in part by FIGS. 3-17, together with related apparatus, all in accordance with this invention.

For example, FIG. 17 shows automatic closure device 172 being delivered with closure delivery device 170. Closure device 172 may include proximal umbrella 174, distal umbrella 178, and connecting shaft 176 therebetween. Delivery rod 171 may be used to advance proximal umbrella 174 from delivery device 170 such that umbrella 174 opens. Balloons 61 and 62 of access device 60 are deflated. Then, both access device 60 and delivery device 170 are withdrawn from heart 10. Umbrella 174 will contact the inner surface of myocardium 40, as shown in FIG. 18. Upon further withdrawal of access device 60 and delivery device 170, distal umbrella 178 will be permitted to deploy. Upon deployment of umbrella 178, the hole formed in myocardium 40 will be sealed. Myocardium 40 may be sealed using any acceptable automatic closure device. Alternatively, myocardium 40 may be sutured closed. Additionally, myocardium 40 may be closed with any known closure device, such as an Amplatzer™ occlusion device, other double-button device, plug, or laser plug.

Bleeding into the space between the myocardium and the pericardium should be prevented. The myocardium can be closed without a need to close the pericardium. However, if the pericardium is to be sealed with the automatic closure device, the seal must be tight enough to prevent bleeding into the void between the two.

The percutaneous femoral access site will also need to be sealed. This may be done with sutures, or with a self-closing device such as an Angioseal™ Hemostatic Puncture Closure Device.

Implantable valves in accordance with the preferred embodiments of the present invention may take on a number of forms. However, the implantable valves will likely exhibit several beneficial characteristics. Implantable valves should preferably be constructed of as little material as possible, and should be easily collapsible. The valve may be radially compressed to a size significantly smaller than its deployed diameter for delivery. The implantable valve or support elements of the valve may contain Gothic arch-type structural support elements to efficiently support and maintain the valve once it is implanted.

The implantable valve may have an outer stent that is installed before deploying the valve structure. Valves manufactured in accordance with the principles of the present invention are preferably constructed of biocompatible materials. Some of the materials may be bioabsorbable, so that shortly after the implantation procedure, only the anchoring device and tissue valve remain permanently implanted. The valve leaflets may be composed of homograph valve tissue, animal tissue, valve rebuild material, pericardium, synthetics, or alloys, such as a thin nitinol mesh.

Implantable valves in accordance with the principles of the present invention may be drug eluding to prevent restenosis by inhibiting cellular division or by preventing reapposition of calcium. The drug may act as an active barrier that prevents the formation of calcium on the valve. Additionally, the drug may stimulate healing of the new valve with the aorta. Furthermore, the implantable valves are preferably treated to resist calcification. The support elements of the implantable valve may be exterior to the valve (e.g., between the new valve tissue and the aorta wall), interior to the valve (e.g., valve tissue is between the support elements and the aorta wall), or may form an endoskeleton of the valve (e.g., support elements of the valve may be within the tissue of the implantable valve).

Figure 24:
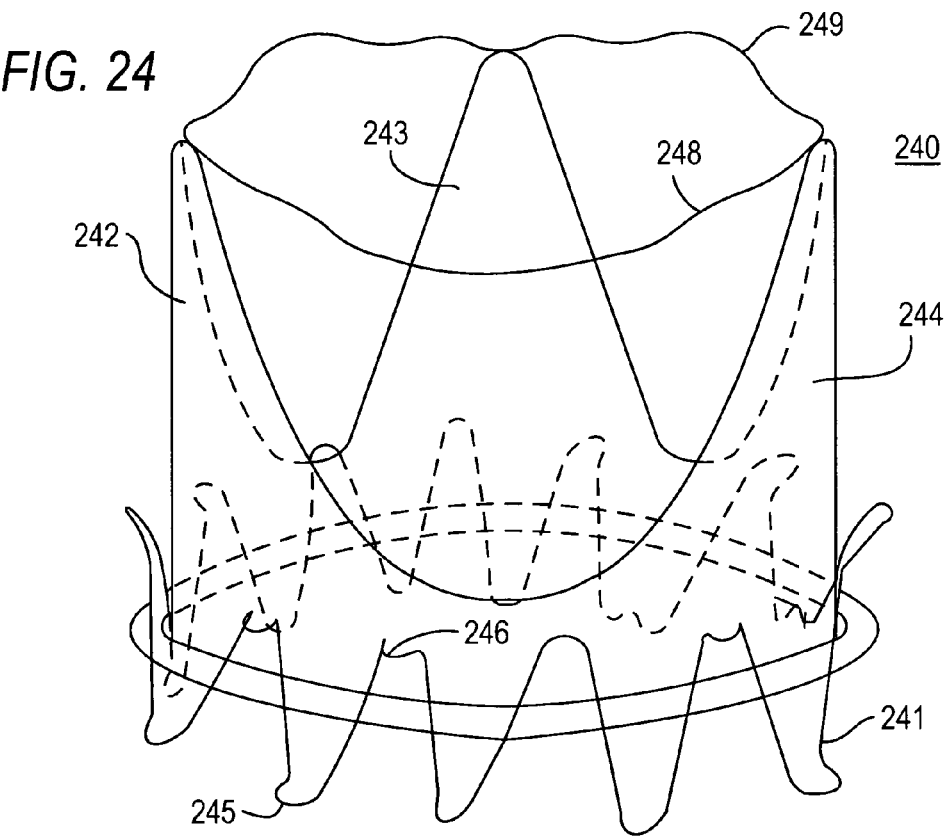
FIG. 24 is a perspective view of an illustrative embodiment of apparatus in accordance with the principles of the present invention.
Figure 25:
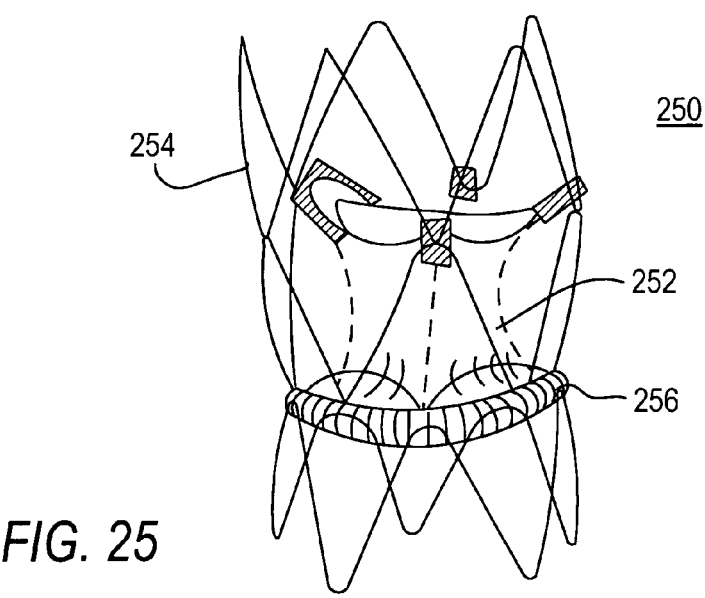
FIG. 25 is a perspective view of an illustrative embodiment of apparatus in accordance with the principles of the present invention.
Figure 26:
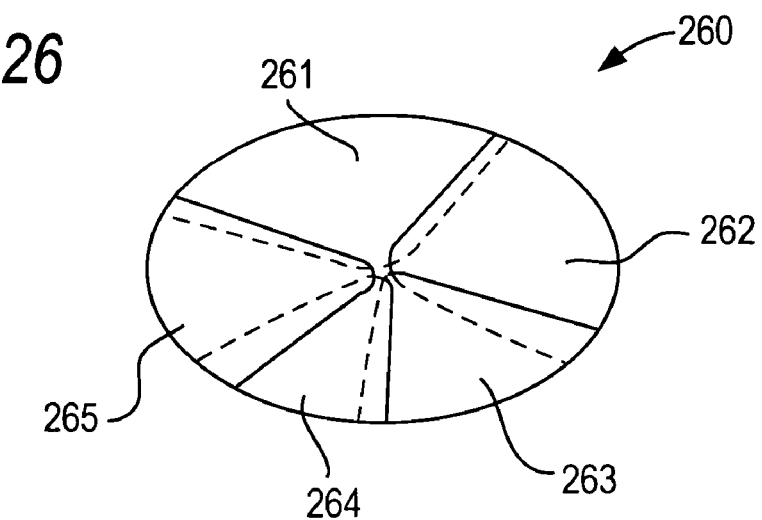
FIG. 26 is a perspective view of an illustrative embodiment of apparatus in accordance with the principles of the present invention.

FIGS. 24-26 illustrate new valves that could be used for replacement or implantation procedures in accordance with the principles of the present invention. Valve 240 of FIG. 24 has sinusoidal attachment member 241 encircling the base of commissure posts 242, 243, and 244. Attachment member 241 may be any radially compressible and expandable member. Member 241 of FIG. 24 has proximal peaks 245 and distal peaks 246 which may be turned outward. Peaks 245 and 246 may be better suited to engage the wall of the aorta when the peaks are turned outward. Peaks 245 and 246 may also be pointed or sharpened so that they penetrate the aorta wall. In embodiments in which a small rim of native valve has been left behind after resection, peaks 245 and 246 may be biased to close outwardly, effectively biting the rim of remaining tissue. Commissure posts 242, 243, and 244 and the valve's leaflets (not shown) fold and collapse when member 241 is radially compressed for delivery.

Valve 240 may have distal mounting ring 248 in some embodiments. Ring 248 may engage the distal portion of the sino-tubular junction. Ring 248 may have segments 249 that are biased radially outward so as to more securely engage the inner wall of the aorta. The replacement valve may be designed to mimic the natural curvature of the sino-tubular junction. This curvature creates a natural bulge, in which the replacement valve may be able to secure itself against dislodgement.

Valve 250 of FIG. 25 shows tissue 252 inside stent frame 254. Tissue 252, which forms the leaflets of the implantable valve may be engineered and/or grown directly inside of stent frame 254. Alternatively, tissue 252 may be glued or sutured to stent frame 254. Stent frame 252 may incorporate peaks that are turned outward that may have pointed or sharpened tips like those described with respect to valve 240 of FIG. 24. Also, ring 256 may have hook features such as hooks 156 of FIG. 15. Stent frame 252 may be constructed from a shape memory or other self-expanding material. Alternatively, stent frame 252 may be constructed from stainless steel or other materials that are balloon expanded or mechanically expanded.

Valve 260 of FIG. 26 illustrates one embodiment of a low profile valve. Such a low profile valve may reduce the likelihood of coronary artery obstruction. Valve 260 may comprise any number of leaflets. Valve 260 is illustratively shown with five leaflets (i.e., leaflets 261, 262, 263, 264 and 265). The leaflets overlap one another in a domino-type arrangement. Leaflet 265 is the top-most leaflet, overlapping the left side of leaflet 264. The right side of leaflet 264 overlaps the left side of leaflet 263, and so on with leaflet 261 being the bottom-most leaflet. The leaflets may be arranged such that they overlap one another in a clockwise or a counterclockwise fashion. Valve 260 may appear to open like the iris of a camera when viewed from the top (as shown in FIG. 26). The leaflets actually rise out of the plane of the valve annulus. However, because of the valve's very low profile, no commissure supports are needed.

Additionally, spiral, or rolled valves may be used in the implantation or replacement procedure. Such valves unwind instead of being radially expanded. Rolled valves are reduced in diameter for percutaneous or minimally invasive implantation by rolling the valve material into a spiral.

Figure 27:
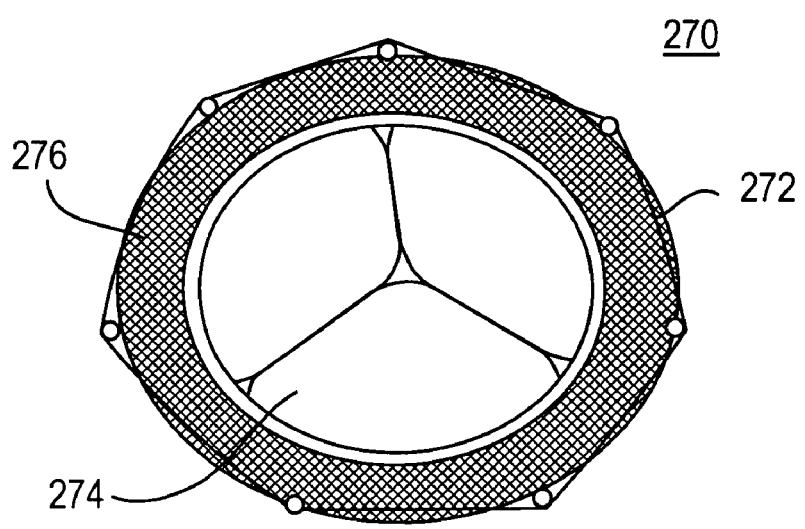
FIG. 27 is a perspective view of an illustrative embodiment of apparatus in accordance with the principles of the present invention.

It may be beneficial to replace an insufficient valve with a new valve that is designed so that it does not dilate to the size of the diseased valve. Insufficient valves do not fully close, permitting regurgitation in the blood flow. This is often the result of a dilated valve annulus, which does not allow the valve leaflets to come together in the center. Therefore, it may be desirable for the new valve to fill a smaller annulus. This can be achieved by designing a valve such as valve 270 of FIG. 27. Valve 270 has fluid-tight membrane 276. Thus, while support structure 272 dilates to the diameter of the diseased valve's annulus, leaflets 274 of the replacement valve operate in an annulus of fixed size determined by membrane 276.

In some embodiments of the present invention, the new valve may be designed to be exchangeable. Many replacement heart valves have a life expectancy of 10-20 years. Therefore, many patients will require follow-up valve replacements. Certain structural components of the heart valve (e.g., the base ring, hooks, etc.) could be permanent, while the tissue leaflets may be exchangeable. It may be preferable to simply dilate the old valve with the new valve.

In some embodiments of the present invention, a valve implantation procedure may take place "off-pump," but the patient's heart may be temporarily arrested. The patient's heart is stopped using fibrillation. A surgeon will have just under three minutes to perform the surgical procedure without risking harm to the patient. However, the anesthetized patient could be cooled to provide the surgeon with more time without increasing the risk for brain damage.

Once the patient's heart is stopped, an incision is made to the aorta just distal to the aortic valve. Blood is cleared from this region so that the surgeon can visualize the valve site. Using a delivery device like that described above (except making a retrograde approach in this case), the new valve is implanted directly over the diseased valve. Because the valve is being installed in a retrograde approach, the native leaflets will be pushed downward before being compressed against the aorta wall. Therefore, there is no concern of coronary artery occlusion.

Once the new valve is installed, the surgical site inside the aorta is cleared of air, and a side bite clamp is placed on the lesion. The heart is restarted with the electrodes that were used to stop it previously. Once the heart is beating again, the clamped lesion is sutured closed. An introducer device (similar to access device 60) can be used at the incision site to prevent the need for clearing the blood from the surgical site and later deairing the site.

There are numerous procedures that may be performed transapically in accordance with the principles of the present invention. The following describes several of the illustrative procedures that may be performed via a transapical access device.

Figure 28:
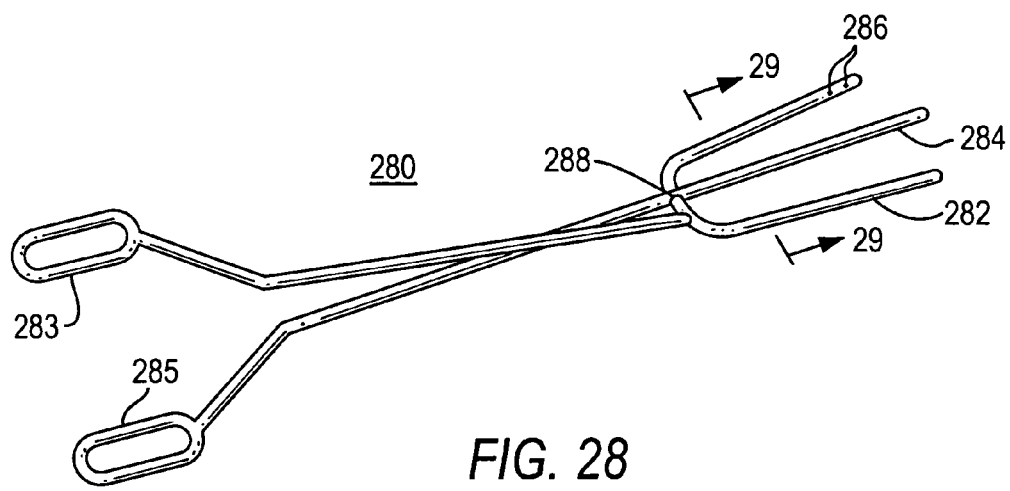
FIG. 28 is a perspective view of an illustrative embodiment of apparatus in accordance with the principles of the present invention.
Figures 29, 30:
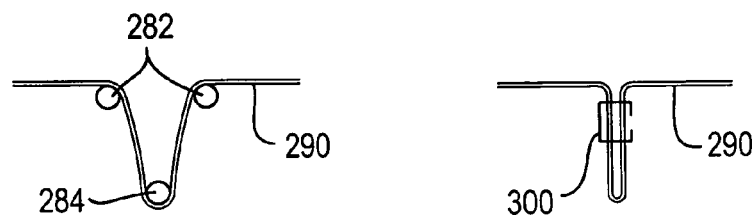
FIG. 29 is a view showing an illustrative procedure incorporating the apparatus of FIG. 28 in accordance with this invention.
FIG. 30 is a view similar to FIG. 29 showing a later stage in the illustrative procedure depicted in part by FIG. 29, together with related apparatus, all in accordance with this invention.

Insufficient mitral valves often result from a dilated posterior leaflet. FIGS. 28-30 demonstrate a tool that could be used to repair an insufficient mitral valve via a transapical access device. Repair tool 280 may have U-shaped head 282 and single-pronged head 284. Heads 282 and 284 may be operably attached by hinge 288. When posterior leaflet 290 (FIG. 29) is inserted between heads 282 and 284, handles 283 and 285 can be squeezed together to cause a portion of posterior leaflet 290 to be drawn downward. At this point, attachment tool 286 can deploy connector 300 (FIG. 30) to retain posterior leaflet 290 in a constrained state, repairing any excess dilation of the mitral annulus. Connector 300 may be a surgical staple, mechanical suture, or other suitable connector.

Figure 31:
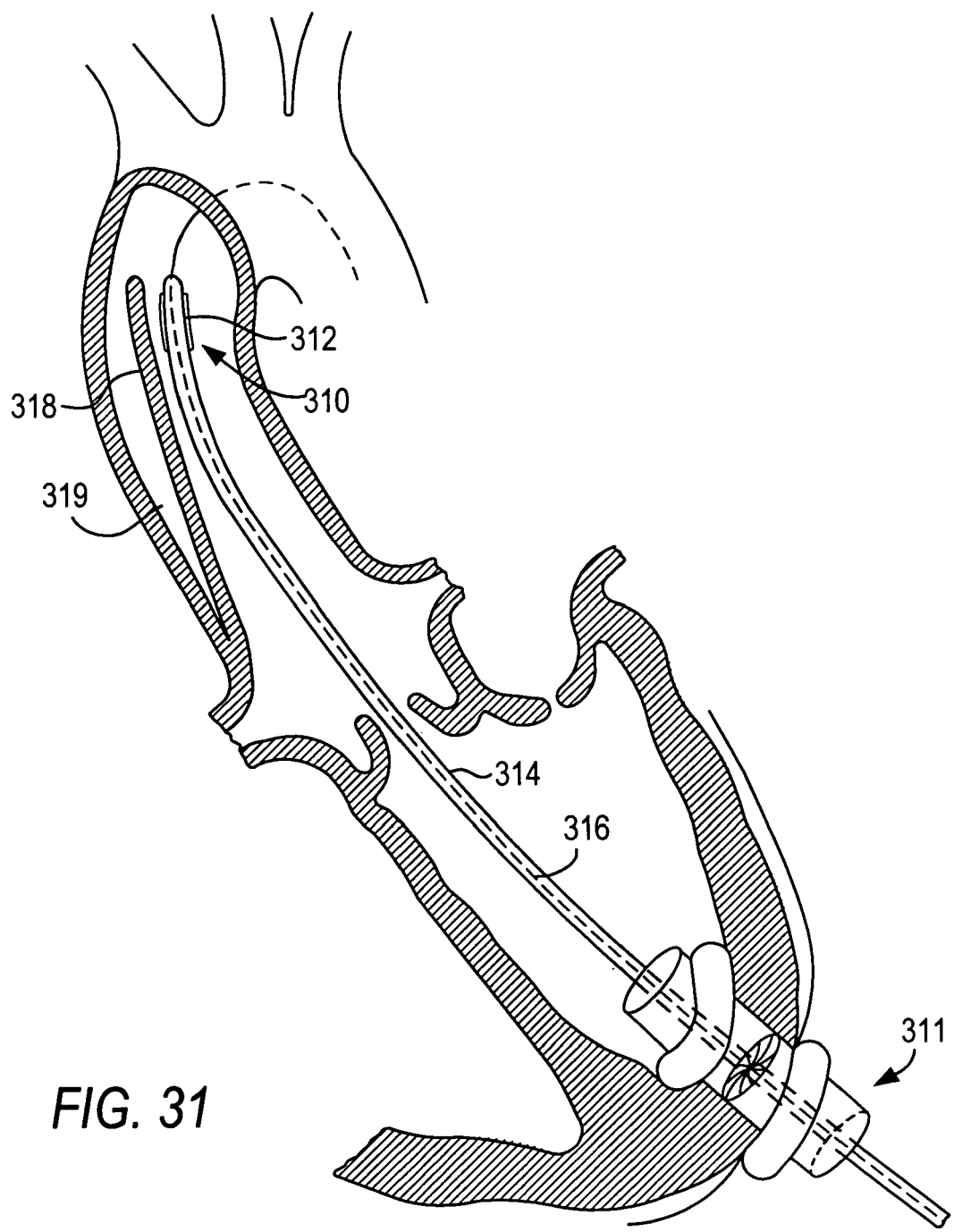
FIG. 31 shows an early stage in an illustrative procedure, together with related apparatus, all in accordance with this invention.

Aortic dissection is another defect that may be repaired via transapical access to the heart. Aortic dissection occurs from a tear or damage to the inner wall of the aorta. Aortic dissection may be caused by traumatic injury or connective tissue diseases such as Marfan syndrome or Ehlers-Danlos syndrome, for example. Aortic dissection may result in atherosclerosis or high blood pressure. As shown in FIG. 31, aortic dissection 318 may result in void 319.

Figure 6:
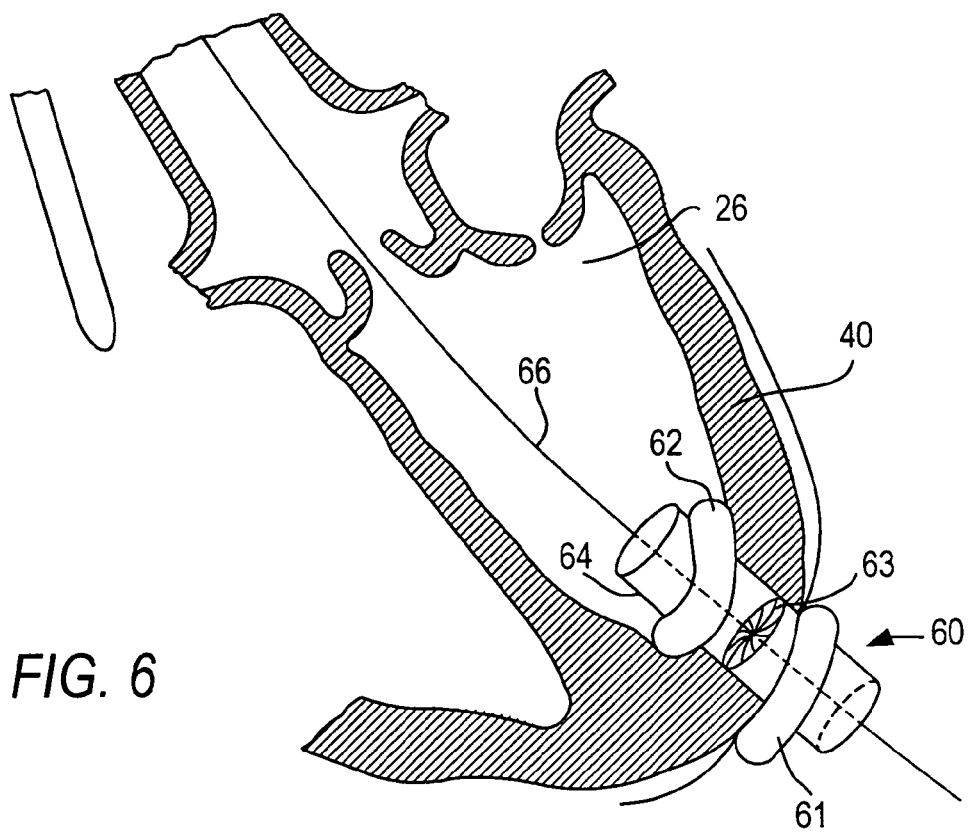
FIG. 6 shows an even later stage in the illustrative procedure depicted in part by FIGS. 3-5, together with related apparatus, all in accordance with this invention.

Aortic dissection repair device 310 may be transapically inserted into a patient via access device 311 (substantially similar to access device 60 of FIG. 6). Repair device 310 may include balloon 312 and catheter 314 and may be guided by guidewire 316. Though not shown, catheter 314 may include several lumens (e.g., a balloon inflation lumen, a guidewire lumen, and a glue delivery lumen).

Figure 32:
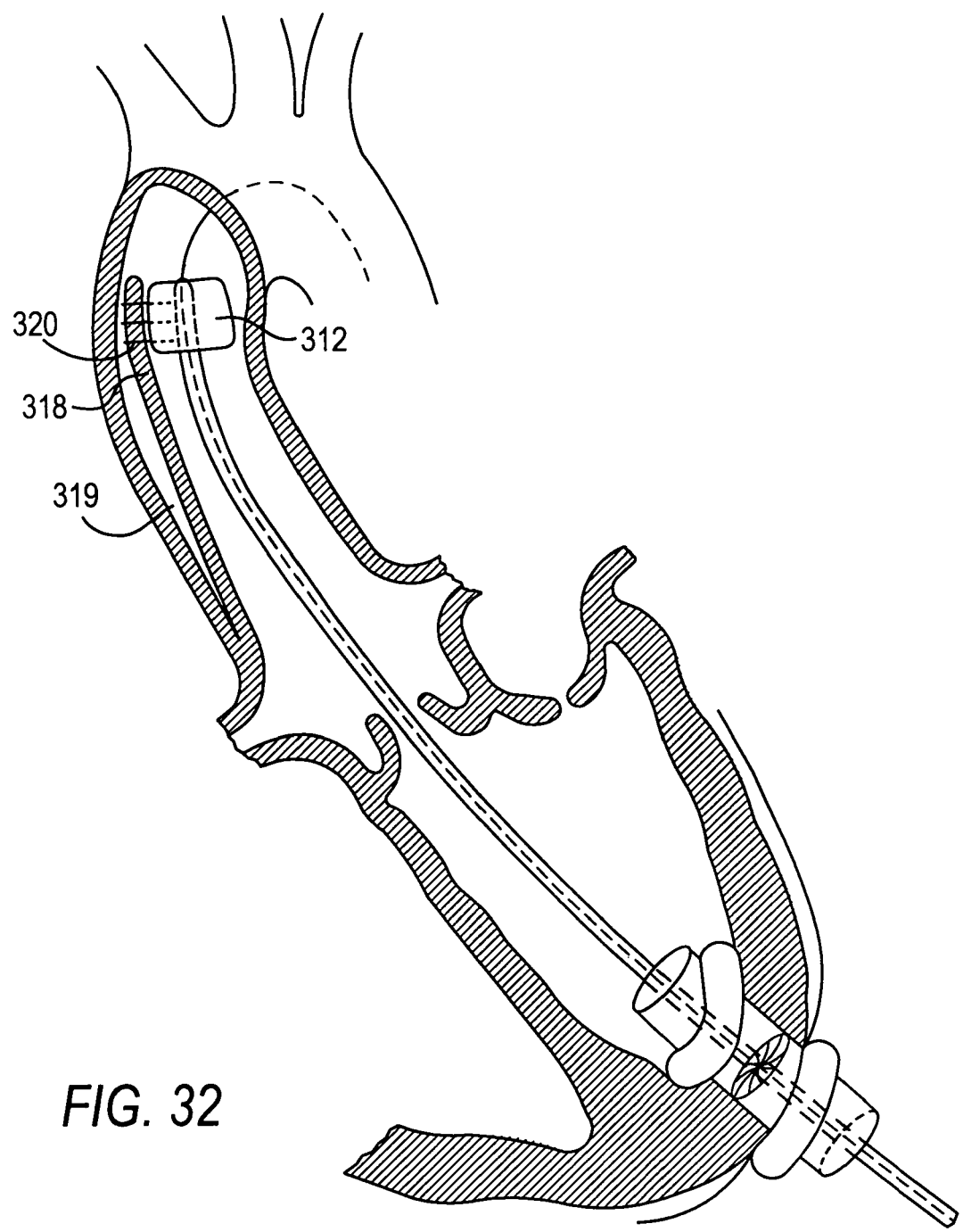
FIG. 32 is a view similar to FIG. 31 showing a later stage in the illustrative procedure depicted in part by FIG. 31, together with related apparatus, all in accordance with this invention.

Once repair device 310 is properly located, balloon 312 may be inflated as shown in FIG. 32. The inflation of balloon 312 may cause needles 320 to penetrate aortic dissection 318 such that the tips of needles 320 are exposed to void 319. A biologically compatible glue may be injected through needles 320 via the glue delivery lumen (not shown) of catheter 314. Further inflation of balloon 312 may ensure that dissection 318 is securely affixed to the aorta wall by the biologically compatible glue.

In order to make sure that the biologically compatible glue is only injected into void 319, and not the remainder of the aorta (which may introduce the biologically compatible glue to the circulatory system), dye may first be injected through select channels (i.e., needles 320). This will allow a surgeon to determine if injected glue would only end up in the desired locations. Repair device 310 may then be rotated to align the needles that will inject the biologically compatible glue with void 319. Alternatively, the needles that will be used to inject the glue may be selectable so that the surgeon activates only the needles aligned with void 319.

Figure 33:
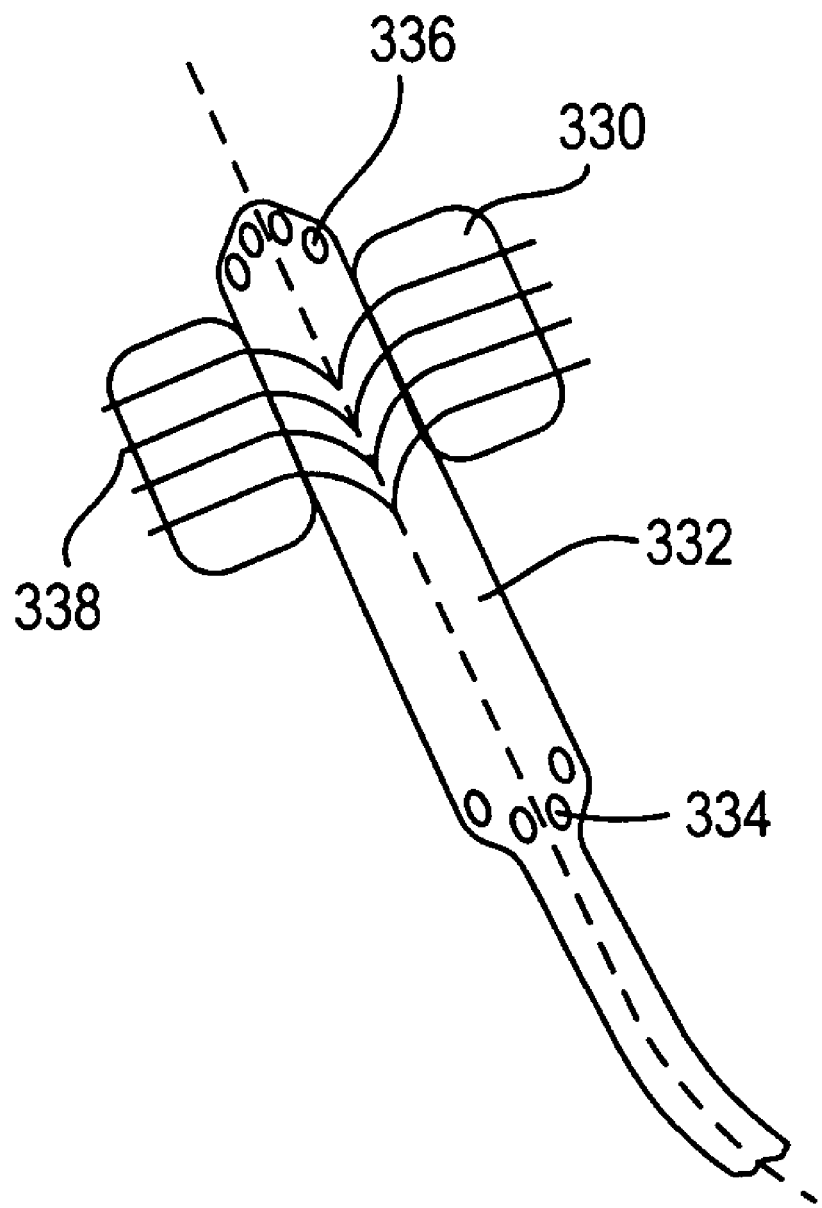
FIG. 33 is a perspective view of an illustrative embodiment of apparatus in accordance with the principles of the present invention.

Because balloon 312 fully occludes the aorta, balloon 312 may be doughnut-shaped to allow blood to pass, like balloon 330 of FIG. 33. Additionally, balloon 330 may include VAD device 332 to pump blood from the proximal side of balloon 330 (at inlet ports 334) to the distal side of balloon 330 (at outlet ports 336). The repair device may still include needles 338. The aortic dissection repair procedure may be monitored with any of the visualization equipment discussed in more detail above. Once the aortic dissection has been repaired, balloon 312 or 330 may be deflated, and repair device 310 is removed from the patient.

Left ventricular aneurysms are another deformity of the heart that may be treated transapically. The heart muscle in the area of a blood vessel blockage can die over time. The healing process may form a scar that could thin and stretch to form a ventricular aneurysm. Such aneurysms may be repaired as described below.

Figure 34:
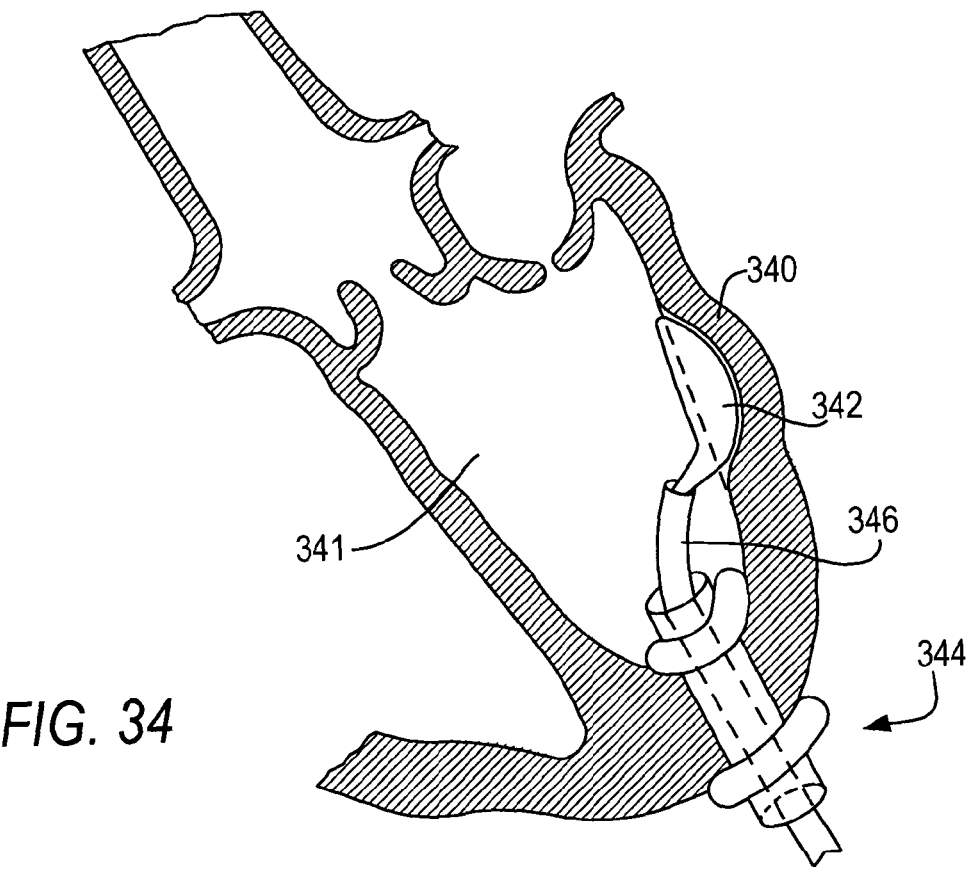
FIG. 34 shows an early stage in an illustrative procedure, together with related apparatus, all in accordance with this invention.

Left ventricular aneurysm 340 may form in left ventricle 341 of a patient, as shown in FIG. 34. Because aneurysm 340 can cause the heart to work harder over time and result in eventual heart failure, the aneurysm should be treated. Aneurysm repair device 336 may be inserted through access device 344 (substantially like access device 60 of FIG. 6). Repair device 346 may include liquid filled bolster 342 that is mounted inside left ventricular aneurysm 340. Bolster 342 may be mounted with a biologically compatible glue, by mechanical means, or by any other suitable mounting technique.

Figure 35:
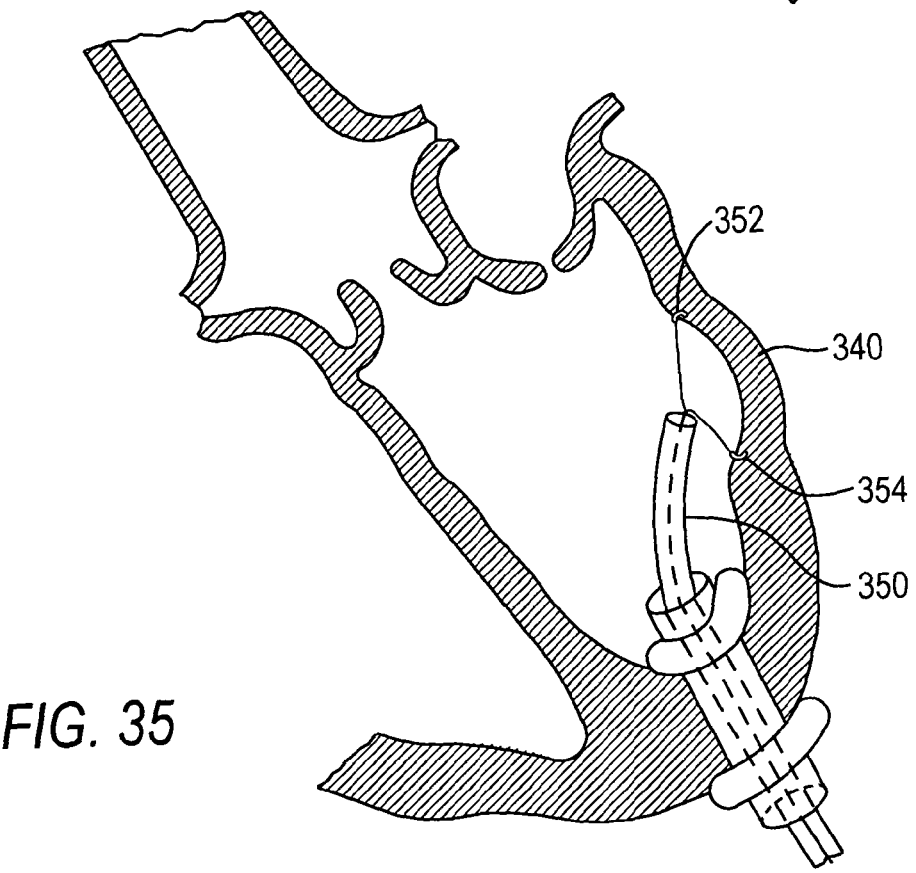
FIG. 35 shows an early stage in an illustrative procedure, together with related apparatus, all in accordance with this invention.

In some embodiments of the present invention, aneurysm 340 may be repaired by pulling the ends of aneurysm 340 together, as depicted by FIG. 35. In such embodiments, aneurysm repair device 350 may be used to deploy hooks 352 and 354. Hooks 352 and 354 may grasp the interior of the heart at the extremes of the aneurysm and then draw the aneurysm closed. Once the aneurysm has been drawn together, any suitable technique can be used to secure the aneurysm in the closed position (e.g., biologically compatible glue, surgical staples, mechanically placed sutures, etc.) Once the aneurysm has been fully sealed, repair device 350 may be withdrawn from the patient.

In some embodiments of the present invention, endoprostheses may be placed percutaneously, transapically, or via any combination of surgical approaches. Endoprostheses may be placed in the ascending aorta that have arms capable of extending into the coronary arteries. Endoprostheses for the ascending aorta could also include a replacement valve or a valved stent. Endoprostheses for the descending aorta could also be placed transapically or percutaneously, for example, to repair an abdominal aortic aneurysm.

Figure 40:
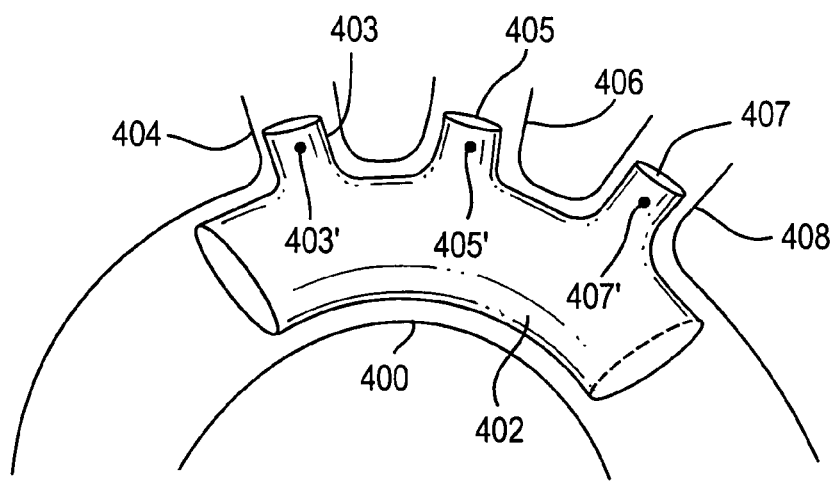
FIG. 40 is a perspective view of an illustrative embodiment of apparatus in accordance with the principles of the present invention.

Additionally, endoprostheses may be placed in the aortic arch. One embodiment of an endoprosthesis for the aortic arch is shown in FIG. 40. Endoprosthesis 402 may be placed in aortic arch 400. Furthermore, endoprosthesis 402 may include arms 403, 405, and 407 that extend into brachiocephalic artery 404, left common carotid artery 406, and left subclavian artery 408, respectively.

Figure 41:
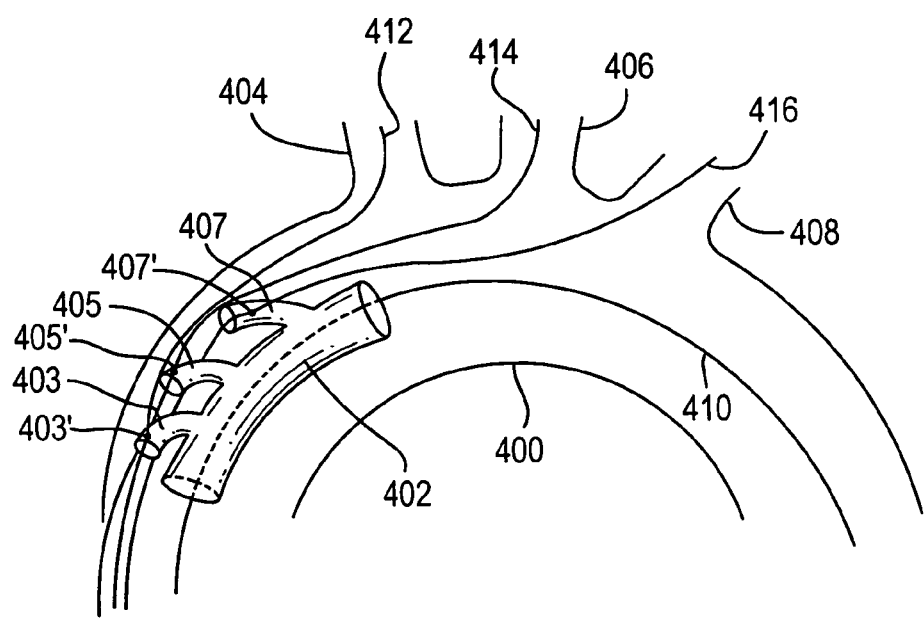
FIG. 41 is a view similar to FIG. 40 showing an earlier stage in an illustrative procedure depicted in part by FIG. 40, together with related apparatus, all in accordance with this invention.

Endoprosthesis 402 may be placed using guidewires 410, 412, 414, and 416, as shown in FIG. 41. Guidewire 410 may pass through the body of endoprosthesis 402, while guidewires 412, 414, and 416 may pass through holes 403', 405', and 407' of the ends of arms 403, 405, and 407, respectively. Once endoprosthesis 402 is properly positioned in aortic arch 400, arms 403, 405, and 407 may be extended to a position substantially perpendicular to the body of endoprostheses 402. In order to aid the insertion of the arms of endoprosthesis 402 into the respective arterial branches, small catheters, or other pushing devices, may be inserted over guidewires 412, 414, and 416 to manipulate (e.g., push) the arms of the endoprosthesis. The arms and body of endoprosthesis 402 may be radially expanded once the endoprosthesis is properly positioned.

Currently, ventricular arrhythmias are percutaneously repaired with radio frequency, cold, heat, or microwave that is applied to the offending tissue to destroy the source of the arrhythmia. Ventricular arrhythmias could be repaired transapically in accordance with the principles of the present invention. Radio frequency, cold, heat, or microwave devices can be introduced through an access device like access device 60 of FIG. 6.

Hypertrophic obstructions (i.e., obstructions distal to a heart valve) and subvalvular stenosis (i.e., an obstruction proximal to a heart valve) may also be treated transapically. Devices such as those described above to resect a diseased valve could be inserted transapically to cut away the hypertrophic or subvalvular obstruction. The extra tissue could be removed from the heart in the same way that the diseased valve is resected and removed.

Robotic technology similar to that currently used in operating rooms could be used to perform some of the steps of the heart valve removal and replacement or implantation procedure. For example, it may be desirable to have a robot perform the delicate resection procedure via the access device. Furthermore, a robot could exercise precision in rotating and positioning the replacement valve with proper alignment of the commissure posts.

Because the heart valve operation is being performed inside one or more of the heart's chambers, all of the equipment described above should be atraumatic to limit damage to the endothelial wall of the heart.

It will be understood that the foregoing is only illustrative of the principles of the invention, and that various modifications can be made by those skilled in the art without departing from the scope and spirit of the invention. For example, the order of some steps in the procedures that have been described are not critical and can be changed if desired. Also, various steps may be performed with various techniques. For example, the diseased valve may be removed transapically, while the replacement valve is implanted percutaneously, or vice versa. The manner in which visualization equipment and techniques are used for observation of the apparatus inside the patient may vary. Many surgical repair procedures can be performed on or near the heart in accordance with the principles of the present invention.

What is claimed is:

1. A method for implanting a heart valve comprising:
   accessing a patient's heart by piercing a myocardium with a cannulated needle having a sharp end;
   feeding through the cannulated needle an elongated wire configured to conform to a direction of blood flow, the feeding continuing such that the wire follows the blood flow until a length of the wire extends at least from a ventricular apex of the heart through an aortic valve of the heart;
   installing an access device in a wall of the heart, the access device having means for preventing bleeding through the access device;
   inserting a valve delivery device through the access device; and
   installing the heart valve.

2. The method of claim 1 further comprising resecting a native heart valve.

3. The method of claim 2 wherein the resecting the native heart valve is performed percutaneously and the installing the heart valve is performed transapically.

4. The method of claim 1 wherein the installing the heart valve further comprises radially expanding the heart valve.

5. The method of claim 1 wherein the installing the heart valve further comprises pulling leaflets of a native heart valve downward.

6. A method of operating on a patient comprising:
   accessing the patient's heart by piercing a myocardium at a ventricular apex of the heart with a cannulated needle having a sharp end;
   feeding through the cannulated needle an elongated wire having a length along which the wire is configured to conform to a direction of blood flow, the feeding directed by the blood flow such that the wire follows the blood flow, the feeding continuing until the length extends at least from the ventricular apex to an aorta;
   installing an access device in a wall of the heart, the access device having means for preventing bleeding through the access device; and
   performing a surgical procedure of implanting a heart valve.

7. The method of claim 6 further comprising resecting a native heart valve.

8. The method of claim 6 wherein installing the access device in the wall of the heart further comprises installing the access device in a ventricular apex of the heart.

9. A method of operating on a patient comprising:
   accessing the patient's heart by piercing a myocardium with a cannulated needle having a sharp end;
   installing an access device in a wall of the heart, the access device having means for preventing bleeding through the access device; and
   after the accessing and before the installing, feeding through the cannulated needle an elongated wire having a length along which the wire is configured to conform to a direction of blood flow, the feeding continuing such that the wire follows the blood flow until the length extends at least from a ventricular apex of the heart to an aorta;
   performing a surgical procedure in antegrade direction, wherein the surgical procedure is selected from the group consisting of implanting a heart valve or and removing, resecting or modifying a native heart valve.

10. The method according to claim 9, wherein the aortic valve is implanted.

11. The method according to claim 10, wherein a guidewire is fed into the left ventricle, and wherein the guidewire is advanced through the aortic valve and into the aorta.

12. The method according to claim 11, wherein the guidewire is further advanced into the iliac or femoral arteries.

13. The method according to claim 12, wherein wire-guided devices are inserted from the antegrade direction.

14. The method according to claim 13, wherein wire-guided devices are inserted from the retrograde direction.

15. The method of claim 9 wherein the feeding continues until a distal end of the elongated wire exits the patient via an artery wall.

16. A method for implanting an endoprosthesis comprising:

accessing a patient's heart by piercing a myocardium with a cannulated needle having a sharp end;

installing an access device in a wall of the heart, the access device having means for preventing bleeding through the access device;

after the accessing and before the installing, feeding through the cannulated needle an elongated wire having a length along which the wire is configured to conform to a direction of blood flow, the feeding directed by the blood flow such that the wire follows the blood flow, the feeding continuing until the length extends at least from a ventricular apex of the heart to an aorta;

inserting an endoprosthesis delivery device through the access device; and installing the endoprosthesis.

* * * * *